(12) United States Patent
Feesche et al.

(10) Patent No.: US 7,807,443 B2
(45) Date of Patent: Oct. 5, 2010

(54) MICROORGANISMS PROVIDING NOVEL GENE PRODUCTS FORMING OR DECOMPOSING POLYAMINO ACIDS

(75) Inventors: Jörg Feesche, Erkrath (DE); Cornelius Bessler, Düsseldorf (DE); Stefan Evers, Mettmann (DE); Karl-Heinz Maurer, Erkrath (DE); Armin Ehrenreich, Göttingen (DE); Birgit Veith, Göttingen (DE); Heiko Liesegang, Höxter (DE); Anke Henne, Solingen (DE); Christina Herzberg, Bilshausen (DE); Gerhard Gottschalk, Nörten-Hardenberg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 11/611,945

(22) Filed: Dec. 18, 2006

(65) Prior Publication Data

US 2007/0190604 A1 Aug. 16, 2007

Related U.S. Application Data

(63) Continuation of application No. PCT/EP2005/006289, filed on Jun. 11, 2005.

(30) Foreign Application Priority Data

Jun. 26, 2004 (DE) ........................ 10 2004 030 938

(51) Int. Cl.
| | |
|---|---|
| C12N 1/21 | (2006.01) |
| C07H 21/00 | (2006.01) |
| C07K 14/00 | (2006.01) |
| C12N 15/00 | (2006.01) |
| C12N 9/00 | (2006.01) |
| C12P 21/00 | (2006.01) |

(52) U.S. Cl. ............... 435/252.31; 435/183; 435/320.1; 435/69.1; 530/350; 536/23.2; 536/23.1

(58) Field of Classification Search ................. 435/183, 435/252.3, 110, 128, 252.33, 252.34, 252.31, 435/252.32; 530/350; 536/23.1, 23.2
See application file for complete search history.

(56) References Cited

FOREIGN PATENT DOCUMENTS

| EP | 0410638 | 1/1991 |
|---|---|---|
| JP | 08308590 | 11/1996 |
| WO | WO9925864 | 5/1999 |
| WO | WO0181597 | 11/2001 |
| WO | WO02055671 | 7/2002 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Jian et al., Biotechnology Letters 28:1241-1246, 2006.*
Riesenberg et al., Applied Microbiology and Biotechnology 51:422-430, 1999.*
M. Ashiuchi et al. "Physiological and biochemical characteristics of poly γ-glutamate synthetase complex of *Bacillus subtilis*" Eur. J, Biochem, vol, 268, pp. 5321-5328 (2001).
Y. Urushibata, et al. "Charactertation of the *Bacillus subtilis ywsC* gene, involved in γ-polyglutamic acid production" in Journal of Bacteriology , vol. 184,No. 2 pp. 337-343 (2002).
T. Suzuki and Y. Tahara "Characterization of the *Bacillus subtilis ywtD* gene whose product is involved in γ-polyglutamic acid degradation" Journal of Bacteriology. vol. 185,No. 7, pp. 2379-2382 (2003).
M. Ashiuchi and H. Misono "Biochemistry and molecular genetics of poly-γ-glutamate synthesis" Appl. Microbiol. Biotechnol, vol. 59, pp. 9-14 (2002).
D. Hannahan, "Studies on transformation on *Escherichia coli* with plasmids" J. Mol. Microbiol. vol, 166, pp. 557-580 (1983).
J. Vehmaanpera, et al., "Genetic manipulation of *Bacillus amyloliquefaciens*", Journal of Biotechnology., vol. 19. pp. 221-240 (1991).
T. J. Gryczan, et al. "Replication and incompatibility properties of plasmid p. E194 in *Bacillus subtillis*", Journal of Bacteriology., vol. 152, pp. 722-735 (1982).
B. Veith. et al. "The complete genome sequence of *Bacillus licheniformis* DSM13, an organism with great industrial potential" Journal of Molecular Microbiology and Biotechnology, vol. 7, No. 4, pp. 204-211 (2004).
Chang & Cohen, "High frequency transformation of *Bacillus subtilis* protoplasts by plasmid DNA," Molec. Gen. Genet vol. 168, pp. 111-115 (1979).
Database Genseq Online, *Bacillus licheniforrnis* DSM 13, complete genome, Retrieved from EBI Accession No. EM_PRO: AE017333, Sep. 21, 2004.
Database Genseq Online, "*Bacillus licheniformis* genomic sequence tag (GST) #2925" Retrieved from EBI Accession No. GSN ABK75634, Aug. 13, 2002.

(Continued)

*Primary Examiner*—Delia M Ramierez
(74) *Attorney, Agent, or Firm*—David P. LeCroy

(57) ABSTRACT

The invention relates to five or four novel genes and the gene products thereof from *Bacillus licheniformis* and sufficiently similar genes and proteins which are involved in vivo in the formation of polyamino acids. The gene in question is ywsC, ywsC', ywtA, ywtB and ywtD or proteins coded thereby. The gene ywsC, ywsC', ywtA and ywtB can be used to improve biotechnological production methods by microorganisms, wherein they are functionally inactivated; the gene ywtD which codes for a peptide decomposing poly-gamma glutamate can, inversely, contribute to the improvement of biotechnological production methods by increased expression. Said genes can be used positively, preferably to result in a modification or decomposition of poly-gamma glutamate.

23 Claims, 14 Drawing Sheets

OTHER PUBLICATIONS

Database Genseq Online "*Bacillus licheniformis* genomic sequence tag (GST) #1706", Retrieved from EBI Accession No. GSN ABK74415, Aug. 13, 2002.

Database EMBL Online, "*Bacillus subtilis ywsC, ywtA, ywtB, ywtC* genes, complete cds." retrieved from EBI accession No. EM_PRO AB046355, Apr. 11, 2001.

Database EMBL Online "Process for producing poly-gamma-glutoamic acid", retrieved from EBI Accession No. EM_PRO: E50424, Feb. 8, 2002.

Database JPO Proteins Online, "Process for producing poly-gamma-glutamic acid.", IP002339841, retrieved from EBI Accession No, JPOP:E82283, Jan. 31, 2002.

Database Geneseg Online, *Bacillus subtilis* IFO 3336 DNA encoding glutamate racemase enzyme XP002339842, retrieved from EBI accession No. GSN:AAF82254.

A. Lapidus, Co-linear scaffold of the *Bacillus licheniformis* and *Bacillus subtilis* genomes and its use to compare their competence genes, Fems Microbilogy Letters, vol. 209, No. 1, pp, 23-30, (2002).

D. Xu et al., "Phylogenetic relationships between *Bacillus* species and related genera inferred from comparison of 3' end 16S rDNA and 5' end 16S-23S ITS nucleotide sequences", International Journal of Systematic and Evolutionary Microbiology, Society for General Microbiology, Reading, GB, vol. 53, No. 3, pp. 695-704, (2003).

G.A, Birrer et al., "γ-Poly(glutamic acid) formation by *Bacillus lichentiformis* 9945a: physiological and biochemical studies", International Journal of Biological Macromolecules. Butterworth & Co., Guildform, GB, vol. 16, No. 5, pp. 265-275, (1995).

A.M., Cromwick et al., "Effects of pH and aeration on γ-poly(glutamic acid) formation by *Bacillus licheniformis* in controlled batch germentor cultures", Biotechnology and Bioengineering Including: Syomposium Biotechnology in Energy Production and Consderation, John Wiley & Sons, NY, vol. 50, pp. 222-227, (1996).

Vivek Anantharaman and L. Aravind, Evolutionary history, structural features and biochemical diversity of the NlpC/P60 superfamily of enzymes, Genome Biology, vol. 4, Issue 2, pp. R11.1 to R1.12, 2003.

\* cited by examiner

Figure 1 / part 1

```
            1                                                    50
B.l. ywsC   ATGAATGAAT TTACATATCA GATTCCAAGA AGGAGATGTA GACAAACAAT
B.s. ywsC   .......... .......... .......... .......... ........AT 51                                                   100
B.l. ywsC   GTGGGTAATG CTATTAGCCT GTGTGATCGT TGTTGGGATC GGCATTTATG
B.s. ywsC   GTGGTTACTC ATTATAGCCT GTGCTGTCAT ACTGGTCATC GGAATATTAG 101                                                  150
B.l. ywsC   AAAAAAGGCG CCACCAGCAA AATATCGATG CGCTGCCTGT CCGAGTGAAC
B.s. ywsC   AAAAACGACG ACATCAGAAA ACATTGATG  CCCTCCCTGT TCGGGTGAAT 151                                                  200
B.l. ywsC   ATCAACGGTA TACGCGGAAA GTCCACGGTG ACAAGATTAA CAACAGGGAT
B.s. ywsC   ATTAACGGCA TCCGCGGAAA ATCGACTGTG ACAAGGCTGA CAACCGGAAT 201                                                  250
B.l. ywsC   ATTAATCGAA GCAGGCTACA AACAGTAGG  AAAAACAACC GGGACAGACG
B.s. ywsC   ATTAATAGAA GCCGGTTACA AGACTGTTGG AAAAACAACA GGAACAGATG 251                                                  300
B.l. ywsC   CAAGGATGAT TTATTGGGAC ACACCGGAAG AGAAGCCGAT CAAAAGAAAG
B.s. ywsC   CAAGAATGAT TTACTGGGAC ACACCGGAGG AAAAGCCGAT TAAACGGAAA 301                                                  350
B.l. ywsC   CCGCAAGGGC CGAATATCGG AGAGCAGAAG GAGGTTATGA AAGAAACGGT
B.s. ywsC   CCTCAGGGGC CGAATATCGG AGAGCAAAAA GAAGTCATGA GAGAAACAGT 351                                                  400
B.l. ywsC   GGAAAGAGGG GCCAATGCGA TTGTCAGTGA GTGCATGGCC GTTAATCCTG
B.s. ywsC   AGAAAGAGGG GCTAACGCGA TTGTCAGTGA ATGCATGGCT GTTAACCCAG 401                                                  450
B.l. ywsC   ATTACCAAAT CATCTTTCAG GAAGAATTGC TTCAGGCTAA TATCGGCGTG
B.s. ywsC   ATTATCAAAT CATCTTTCAG GAAGAACTTC TGCAGGCCAA TATCGGCGTC 451                                                  500
B.l. ywsC   ATCGTGAACG TGCTGGAGGA TCACATGGAT GTGATGGGAC CGACTTTGGA
B.s. ywsC   ATTGTGAATG TTTTGGAAGA CCATATGGAT GTCATGGGGC CGACGCTTGA 501                                                  550
B.l. ywsC   TGAAATCGCA GAAGCATTCA CAGCAACCAT TCCTTATAAT GGACATTTGG
B.s. ywsC   TGAAATTGCA GAAGCGTTTA CTGCTACAAT TCCTTATAAT GGCCATCTTG 551                                                  600
B.l. ywsC   TTATTACTGA TAGTGAGTAT ACCGATTTCT TAAGCAAAT  TGCAAAGAA
B.s. ywsC   TCATTACAGA TAGTGAATAT ACCGAGTTCT TAAACAAAA  AGCAAAGAA 601                                                  650
B.l. ywsC   AGGAACACAA AAGTCATCGT CGCAGACAAT TCTAAAATAA CAGATGAATA
B.s. ywsC   CGAAACACAA AAGTCATCAT TGCTGATAAC TCAAAAATTA CAGATGAGTA
```

Figure 1 / part 2

```
               651                                                                 700
B.l. ywsC      CCTCAGACAG TTTGAGTACA TGGTATTCCC TGATAATGCG TCTCTTGCGC
B.s. ywsC      TTTACGTAAA TTTGAATACA TGGTATTCCC TGATAACGCT TCTCTGGCGC 701                                                                 750
B.l. ywsC      TCGGTGTAGC TCAAGCGTTG GGCATTGACG AAGAAACCGC CTTTAAAGGC
B.s. ywsC      TGGGTGTGGC TCAAGCACTC GGCATTGACG AAGAAACAGC ATTTAAGGGA 751                                                                 800
B.l. ywsC      ATGCTGAATG CGCCGCCTGA TCCGGGAGCC ATGAGAATTC TGCCGCTGAT
B.s. ywsC      ATGCTGAATG CGCCGCCAGA TCCGGGAGCA ATGAGAATTC TTCCGCTGAT 801                                                                 850
B.l. ywsC      GAACGCCAAG AATCCCGGAC ATTTCGTCAA CGGTTTTGCG GCCAATGACG
B.s. ywsC      CAGTCCGAGC GAGCCTGGGC ACTTTGTTAA TGGGTTTGCC GCAAACGACG 851                                                                 900
B.l. ywsC      CAGCTTCCAC TTTAAACATT TGGAAGCGTG TAAAAGAAAT AGGCTATCCT
B.s. ywsC      CTTCTTCTAC TTTGAATATA TGGAAACGTG TAAAAGAAAT CGGTTACCCG 901                                                                 950
B.l. ywsC      ACGGATCAGC CGATCGTCAT TATGAACTGC CGCGCCGACA GGGTAGACAG
B.s. ywsC      ACCGATGATC CGATCATCAT CATGAACTGC CGCGCAGACC GTGTCGATCG 951                                                                1000
B.l. ywsC      AACACAGCAG TTTGCGGAAG ATGTCCTTCC TTATATTGAA GCAAGTGAAC
B.s. ywsC      GACACAGCAA TTCGCAAATG ACGTATTGCC TTATATTGAA GCAAGTGAAC 1001                                                                1050
B.l. ywsC      TTGTGCTGAT TGGAGAAACA ACAGAGCCGA TCGTCAAAGC ATATGAAGCA
B.s. ywsC      TGATCTTAAT CGGTGAAACA ACAGAACCGA TCGTAAAAGC CTACGAAGAA 1051                                                                1100
B.l. ywsC      GGCAAAATTC CTGCGGACAA GCTGTTTGAT TTTGAGCACA AATCAACGGA
B.s. ywsC      GGCAAAATTC CTGCAGACAA ACTGCATGAT CTAGAGTATA AGTCAACAGA 1101                                                                1150
B.l. ywsC      AGAAATCATG TTCATGCTGA AAAACAAGCT TGAGGGCCGC GTTATTTACG
B.s. ywsC      TGAAATTATG GAATTGTTAA AGAAAGTAT GCACAACCGT GTCATATATG 1151                                                                1200
B.l. ywsC      GAGTCGGAAA TATCCACGGA GCAGCGGAGC CTCTCATTGA AAAAATACAA
B.s. ywsC      GCGTCGGCAA TATTCATGGT GCCGCAGAGC CTTTAATTGA AAAAATCCAC 1201                                         1230
B.l. ywsC      GATTACAAGA TTAAGCAGCT CGTTAGCTAG
B.s. ywsC      GAATACAAGG TAAAGCAGCT CGTAAGC...
```

Figure 2 / part 1

```
              1                                                          50
B.l. ywsC'    ATGTGGGTAA TGCTATTAGC CTGTGTGATC GTTGTTGGGA TCGGCATTTA
B.s. ywsC     ATGTGGTTAC TCATTATAGC CTGTGCTGTC ATACTGGTCA TCGGAATATT 51                                                         100
B.l. ywsC'    TGAAAAAAGG CGCCACCAGC AAAATATCGA TGCGCTGCCT GTCCGAGTGA
B.s. ywsC     AGAAAAACGA CGACATCAGA AAAACATTGA TGCCCTCCCT GTTCGGGTGA 101                                                        150
B.l. ywsC'    ACATCAACGG TATACGCGGA AAGTCCACGG TGACAAGATT AACAACAGGG
B.s. ywsC     ATATTAACGG CATCCGCGGA AAATCGACTG TGACAAGGCT GACAACCGGA 151                                                        200
B.l. ywsC'    ATATTAATCG AAGCAGGCTA CAAAACAGTA GGAAAAACAA CCGGGACAGA
B.s. ywsC     ATATTAATAG AAGCCGGTTA CAAGACTGTT GGAAAAACAA CAGGAACAGA 201                                                        250
B.l. ywsC'    CGCAAGGATG ATTTATTGGG ACACACCGGA AGAGAAGCCG ATCAAAGAA
B.s. ywsC     TGCAAGAATG ATTTACTGGG ACACACCGGA GGAAAAGCCG ATTAAACGGA 251                                                        300
B.l. ywsC'    AGCCGCAAGG GCCGAATATC GGAGAGCAGA AGGAGGTTAT GAAAGAAACG
B.s. ywsC     AACCTCAGGG GCCGAATATC GGAGAGCAAA AGAAGTCAT GAGAGAAACA 301                                                        350
B.l. ywsC'    GTGGAAAGAG GGGCCAATGC GATTGTCAGT GAGTGCATGG CCGTTAATCC
B.s. ywsC     GTAGAAAGAG GGGCTAACGC GATTGTCAGT GAATGCATGG CTGTTAACCC 351                                                        400
B.l. ywsC'    TGATTACCAA ATCATCTTTC AGGAAGAATT GCTTCAGGCT AATATCGGCG
B.s. ywsC     AGATTATCAA ATCATCTTTC AGGAAGAACT TCTGCAGGCC AATATCGGCG 401                                                        450
B.l. ywsC'    TGATCGTGAA CGTGCTGGAG GATCACATGG ATGTGATGGG ACCGACTTTG
B.s. ywsC     TCATTGTGAA TGTTTTGGAA GACCATATGG ATGTCATGGG GCCGACGCTT 451                                                        500
B.l. ywsC'    GATGAAATCG CAGAAGCATT CACAGCAACC ATTCCTTATA ATGGACATTT
B.s. ywsC     GATGAAATTG CAGAAGCGTT TACTGCTACA ATTCCTTATA ATGGCCATCT 501                                                        550
B.l. ywsC'    GGTTATTACT GATAGTGAGT ATACCGATTT CTTTAAGCAA ATTGCAAAAG
B.s. ywsC     TGTCATTACA GATAGTGAAT ATACCGAGTT CTTTAAACAA AAAGCAAAAG 551                                                        600
B.l. ywsC'    AAAGGAACAC AAAAGTCATC GTCGCAGACA ATTCTAAAAT AACAGATGAA
B.s. ywsC     AACGAAACAC AAAAGTCATC ATTGCTGATA ACTCAAAAAT TACAGATGAG
```

Figure 2 / part 2

```
             601                                                    650
B.l. ywsC'   TACCTCAGAC AGTTTGAGTA CATGGTATTC CCTGATAATG CGTCTCTTGC
B.s. ywsC    TATTTACGTA AATTTGAATA CATGGTATTC CCTGATAACG CTTCTCTGGC 651                                                    700
B.l. ywsC'   GCTCGGTGTA GCTCAAGCGT TGGGCATTGA CGAAGAAACC GCCTTTAAAG
B.s. ywsC    GCTGGGTGTG GCTCAAGCAC TCGGCATTGA CGAAGAAACA GCATTTAAGG 701                                                    750
B.l. ywsC'   GCATGCTGAA TGCGCCGCCT GATCCGGGAG CCATGAGAAT TCTGCCGCTG
B.s. ywsC    GAATGCTGAA TGCGCCGCCA GATCCGGGAG CAATGAGAAT TCTTCCGCTG 751                                                    800
B.l. ywsC'   ATGAACGCCA AGAATCCCGG ACATTTCGTC AACGGTTTTG CGGCCAATGA
B.s. ywsC    ATCAGTCCGA GCGAGCCTGG GCACTTTGTT AATGGGTTTG CCGCAAACGA 801                                                    850
B.l. ywsC'   CGCAGCTTCC ACTTTAAACA TTTGGAAGCG TGTAAAAGAA ATAGGCTATC
B.s. ywsC    CGCTTCTTCT ACTTTGAATA TATGGAAACG TGTAAAAGAA ATCGGTTACC 851                                                    900
B.l. ywsC'   CTACGGATCA GCCGATCGTC ATTATGAACT GCCGCGCCGA CAGGGTAGAC
B.s. ywsC    CGACCGATGA TCCGATCATC ATCATGAACT GCCGCGCAGA CCGTGTCGAT 901                                                    950
B.l. ywsC'   AGAACACAGC AGTTTGCGGA AGATGTCCTT CCTTATATTG AAGCAAGTGA
B.s. ywsC    CGGACACAGC AATTCGCAAA TGACGTATTG CCTTATATTG AAGCAAGTGA 951                                                   1000
B.l. ywsC'   ACTTGTGCTG ATTGGAGAAA CAACAGAGCC GATCGTCAAA GCATATGAAG
B.s. ywsC    ACTGATCTTA ATCGGTGAAA CAACAGAACC GATCGTAAAA GCCTACGAAG 1001                                                   1050
B.l. ywsC'   CAGGCAAAAT TCCTGCGGAC AAGCTGTTTG ATTTTGAGCA CAAATCAACG
B.s. ywsC    AAGGCAAAAT TCCTGCAGAC AAACTGCATG ATCTAGAGTA TAAGTCAACA 1051                                                   1100
B.l. ywsC'   GAAGAAATCA TGTTCATGCT GAAAAACAAG CTTGAGGGCC GCGTTATTTA
B.s. ywsC    GATGAAATTA TGGAATTGTT AAAGAAAAGT ATGCACAACC GTGTCATATA 1101                                                   1150
B.l. ywsC'   CGGAGTCGGA AATATCCACG GAGCAGCGGA GCCTCTCATT GAAAAATAC
B.s. ywsC    TGGCGTCGGC AATATTCATG GTGCCGCAGA GCCTTTAATT GAAAAATCC 1151                              1182
B.l. ywsC'   AAGATTACAA GATTAAGCAG CTCGTTAGCT AG
B.s. ywsC    ACGAATACAA GGTAAAGCAG CTCGTAAGC. ..
```

Figure 3

```
               1                                                     50
B.l. ywtA      ATGTTTGGAT CAGATTTATA TATCGCCCTC ATTTTAGGAG TCTTACTCAG
B.s. ywtA      ATGTTCGGAT CAGATTTATA CATCGCACTA ATTTTAGGTG TACTACTCAG 51                                                    100
B.l. ywtA      TTTGATTTTT GCAGAGAAAA CGGGAATTGT ACCAGCCGGC CTCGTCGTAC
B.s. ywtA      TTTAATTTTT GCGGAAAAAA CAGGGATCGT GCCGGCAGGA CTTGTTGTAC 101                                                   150
B.l. ywtA      CGGGTTATTT GGGACTTGTC TTCAATCAGC CGATTTTCAT GCTGCTCGTT
B.s. ywtA      CGGGATATTT AGGACTTGTG TTAATCAGC CGGTCTTTAT TTTACTTGTT 151                                                   200
B.l. ywtA      CTTTTTGTCA GTTTGCTGAC GTATGTCATC GTGAAATTCG GACTTTCCAA
B.s. ywtA      TTGCTAGTGA GCTTGCTCAC GTATGTCATT GTGAAATACG GTTTATCCAA 201                                                   250
B.l. ywtA      AATTATGATT CTATACGGAC GCAGAAAATT CGCAGCAATG CTGATTACGG
B.s. ywtA      ATTTATGATT TTGTACGGAC GCAGAAAATT CGCTGCCATG CTGATAACAG 251                                                   300
B.l. ywtA      GAATTCTTTT GAAAATCGGT TTTGATTTTA TATATCCGGT GATGCCGTTT
B.s. ywtA      GGATCGTCCT AAAAATCGCG TTTGATTTTC TATACCCGAT TGTACCATTT 301                                                   350
B.l. ywtA      GAGATTGCCG AATTCAGGGG AATCGGAATC ATCGTGCCGG GGCTGATCGC
B.s. ywtA      GAAATCGCAG AATTTCGAGG AATCGGCATC ATCGTGCCAG GTTTAATTGC 351                                                   400
B.l. ywtA      CAATACCATT CAAAGACAGG GATTAACGAT TACGCTTGGA AGTACGCTTT
B.s. ywtA      CAATACCATT CAGAAACAAG GTTTAACCAT TACGTTCGGA AGCACGCTGC 401                                                   450
B.l. ywtA      TATTGAGCGG AGCAACATTC GTCATTATGT ATGCTTACTA TCTAATCTAA
B.s. ywtA      TATTGAGCGG AGCGACCTTT GCTATCATGT TTGTTTACTA CTTAATT...
```

Figure 4 / part 1

```
               1                                                      50
B.l. ywtB     ATGAAAAAAC AACTGAACTT TCAGGAAAAA CTGCTGAAGT TGACGAAGCA
B.s. ywtB     ATGAAAAAAG AACTGAGCTT TCATGAAAAG CTGCTAAAGC TGACAAAACA 51                                                     100
B.l. ywtB     GGAGAAAAAG AAAACAAACA AGCACGTCTT TATCGTATTG CCCGTTATTT
B.s. ywtB     GCAAAAAAAG AAAACCAATA AGCACGTATT TATTGCCATT CCGATCGTTT 101                                                    150
B.l. ywtB     TCTGTTTAAT GTTTGTCTTT ACTTGGGTCG GAAGCGCCAA AACTCCTTCG
B.s. ywtB     TTGTCCTTAT GTTCGCTTTC ATGTGGGCGG GAAAAGCGGA AACGCC...G 151                                                    200
B.l. ywtB     CAAATGGACA AAAAGAAGA TGCCAAGCTT ACAGCTACTT TTGTTGGCGA
B.s. ywtB     AAGGTCAAAA CGTATTCTGA CGACGTACTC TCAGCCTCAT TTGTAGGCGA 201                                                    250
B.l. ywtB     TATCATGATG GGAAGAAACG TAGAAAAAGT GACAAACTTG CACGGTTCGG
B.s. ywtB     TATTATGATG GGACGCTATG TTGAAAAAGT AACGGAGCAA AAAGGGGCAG 251                                                    300
B.l. ywtB     AAAGTGTCTT CAAAAATGTG AAGCCGTACT TTAATGTGTC AGATTTTATC
B.s. ywtB     ACAGTATTTT TCAATATGTT GAACCGATCT TTAGAGCCTC GGATTATGTA 301                                                    350
B.l. ywtB     ACAGGAAACT TTGAAAACCC TGTAACCAAT GCAAAGGACT ATCAAGAGGC
B.s. ywtB     GCAGGAAACT TTGAAAACCC GGTAACCTAT CAAAAGAATT ATAAACAAGC 351                                                    400
B.l. ywtB     AGAAAAGAAC ATCCATCTGC AAACGAATCA AGAATCAGTC GAAACATTGA
B.s. ywtB     AGATAAAGAG ATTCATCTGC AGACGAATAA GGAATCAGTG AAAGTCTTGA 401                                                    450
B.l. ywtB     AAAAGCTGAA CTTCAGCGTA CTGAATTTTG CCAACAACCA TGCGATGGAC
B.s. ywtB     AGGATATGAA TTTCACGGTT CTCAACAGCG CCAACAACCA CGCAATGGAT 451                                                    500
B.l. ywtB     TACGGGGAAG ACGGTTTGAA GGATACGCTC AATAAATTTT CAAATGAGAA
B.s. ywtB     TACGGCGTTC AGGGCATGAA AGATACGCTT GGAGAATTTG CGAAGCAAAA 501                                                    550
B.l. ywtB     TCTGGAGCTT GTCGGAGCAG AAATAATCT TGAAGACGCG AAACAGCACG
B.s. ywtB     TCTTGATATC GTTGGAGCGG GATACAGCTT AAGTGATGCG AAAAAGAAAA 551                                                    600
B.l. ywtB     TATCCTATCA GAATGTGAAC GGCGTAAAAA TTGCAACGCT CGGTTTTACA
B.s. ywtB     TTTCGTACCA GAAAGTCAAC GGGGTAACGA TTGCGACGCT TGGCTTTACC
```

Figure 4 / part 2

```
              601                                                          650
B.l. ywtB     GACGTCTACA CAAAGAACTT TACAGCCAAA AAGAACAGAG GCGGAGTGCT
B.s. ywtB     GATGTGTCCG GGAAAGGTTT CGCGGCTAAA AAGAATACGC CGGGCGTGCT 651                                                          700
B.l. ywtB     GCCGCTCAG. TCCGAAAATC TTTATTCCAA TGATTGCGGA AGCATCGAAA
B.s. ywtB     GCC.CGCAGA TCCTGAAATC TTCATCCCTA TGATTTCAGA AGCGAAAAAA 701                                                          750
B.l. ywtB     AAAGCGGATC TTGTCCTTGT CCATGTGCAC TGGGGACAAG AATATGACAA
B.s. ywtB     CATGCGGACA TTGTTGTTGT GCAGTCACAC TGGGGACAAG AGTATGACAA 751                                                          800
B.l. ywtB     TGAACCGAAC GACAGACAGA AGGATCTGGC CAAGGCGATT GCAGATGCCG
B.s. ywtB     TGATCCAAAT GACCGCCAGC GCCAGCTTGC AAGAGCCATG TCTGATGCGG 801                                                          850
B.l. ywtB     GAGCAGATGT CATCATCGGC GCTCATCCCC ATGTTCTCGA ACCGATCGAA
B.s. ywtB     GAGCTGACAT CATCGTCGGC CATCACCCGC ACGTCTTAGA ACCGATTGAA 851                                                          900
B.l. ywtB     GTGTATAACG GTACTGTGAT TTTCTACAGC CTCGGCAACT TTGTATTTGA
B.s. ywtB     GTATATAACG GAACCGTCAT TTTCTACAGC CTCGGCAACT TTGTCTTTGA 901                                                          950
B.l. ywtB     TCAGGGCTGG TCAAGAACAC GGGACAGCGC GCTTGTACAA TACCATTTAA
B.s. ywtB     CCAAGGCTGG ACGAGAACAA GAGACAGTGC ACTGGTTCAG TATCACCTGA 951                                                         1000
B.l. ywtB     TGAATGACGG CAAAGGGCGC TTTGAGGTAA CGCCTCTCAA CATTCGCGAA
B.s. ywtB     AGAAAAATGG AACAGGACGC TTTGAAGTGA CACCGATCGA TATCCATGAA 1001                                                        1050
B.l. ywtB     GCAACGCCGA CGCCTTTAGG CAAGAGCGAC TTCTTAAAAC GAAAAGCGAT
B.s. ywtB     GCGACACCTG CGCCT...GT GAAAAAGAC AGCCTTAAAC AGAAAACCAT 1051                                                        1100
B.l. ywtB     CTTCCGTCAA TTGACAAAAG GAACAAACCT CGACTGGAAA GAAGAGAACG
B.s. ywtB     TATTCGCGAA CTGACGAAAG ACTCTAATTT CGCTTGGAAA GTAGAAGACG 1101                                                        1150
B.l. ywtB     GAAAATTAAC GTTTGAAGTC GATCATGCGG ACAAGCTGAA AAATAATAAA
B.s. ywtB     GAAAACTGAC GTTTGATATT GATCATAGTG ACAAACTAAA ATCTAAA...

1151           1171
B.l. ywtB     AACGGAGTGG TGAACAAATG A
B.s. ywtB     .......... .......... .
```

Figure 5 / part 1

```
                1                                                         50
B.l. ywtD    TTGATAAAAA AAGCGGCAAA CAAAAAGTTG GTTTTGTTTT GTGGAATTGC
B.s. ywtD    ...GTGAACA CACTGGCAAA CTGGAAGAAG TTTTTGCTTG TGGCGGTTAT 51                                                        100
B.l. ywtD    GGTGCTTTGG ATGTCTTTAT TTTTAACGAA TCATAATGAT GTACGCGCCG
B.s. ywtD    CATTTGTTTT TTGGTTCCAA TTATGACAAA AGCGGAGATT GCGGAAGCTG 101                                                       150
B.l. ywtD    ATACGATCGG CGAGAAAATA GCGGAAACT. .GCCAGACAG CTTGAGGGTG
B.s. ywtD    ATAC.ATCAT C.AGAATTGA TTGTCAGCGA AGCAAAAAAC CTGCTTGGAT 151                                                       200
B.l. ywtD    CGAAATACAG CTACGGCGGA GAGAAGCCGA AAACGGGGTT TGACTCGTCA
B.s. ywtD    ATCAGTATAA ATATGGCGGG GAAACGCCGA AGAGGGTTT CGATCCATCA 201                                                       250
B.l. ywtD    GGCTTTGTGC AATATGTGTT TCAATCGCTC GATATTACGC TTCCGAGAAC
B.s. ywtD    GGATTGATAC AATATGTGTT CAGTAAGGCT GATATTCATC TGCCGAGATC 251                                                       300
B.l. ywtD    GGTAAAGGAA CAATCGACTC TTGGGAGCAG TGTCGGCCGT CAGCAGCTCG
B.s. ywtD    TGTAAACGAC CAGTATAAAA TCGGAACAGC TGTAAAACCG GAAAACCTGA 301                                                       350
B.l. ywtD    AAAAGGGGGA CCTTGTCTTT TTCAAGAATG CCGAGCTGGA ATCGGACGGA
B.s. ywtD    AGCCGGGTGA TATTTTGTTT TTCAAGAAAG A.GGGAAGCA CCGGCACTGT 351                                                       400
B.l. ywtD    .CCGACCCAT GTCGCCATCT ATTTGGGAAA TGATCAAATC ATCCACAGCA
B.s. ywtD    TCCGACACAT GACGCCCTTT ATATCGGAGA CGGCCAAATG GTTCACAGTA 401                                                       450
B.l. ywtD    CAAAATCAAA CGGGGTTGTC GTGACAAAGC TTGAAGGCAG CTCTTACTGG
B.s. ywtD    CACAGTCAAA AGGGGTTATC ATCACCAATT ACAAAAAAG CAGCTATTGG 451                                                       500
B.l. ywtD    AGCTCGGGGT ATTTTAAAGC GAAAAGGATC ACAAAAGAGC CTGAGATTTC
B.s. ywtD    AGCGGAACTT ATATCGGGGC GAGACGAATC GCTGCCGATC CGGCAACGGC 501                                                       550
B.l. ywtD    GATGGATCCT GTCGTTCAAA AAGCAAAAAG CTATGTCGGT GTTCCTTATG
B.s. ywtD    TGATGTTCCT GTCGTTCAGG AGGCCGAAAA ATATATCGGT GTCCCATATG 551                                                       600
B.l. ywtD    TATTTGGAGG CAACTCTCCG GATCTCGGAT TTGACTGTTC GGGGTTGACC
B.s. ywtD    TGTTTGGCGG AAGCACGCCG TCAGAGGGCT TGATTGCTC GGGGCTTGTG 601                                                       650
B.l. ywtD    CAATACGTCT TCAGAGAGGT GCTCGGCGTT TATTTGCCAA GGTCGGCTGA
B.s. ywtD    CAATATGTGT TCAACAGGC ACTCGGCATT TATCTACCGC GATCAGCCGA
```

Figure 5 / part 2

```
                651                                              700
B.l. ywtD   ACAGCAATGG GCTGTCGGTC AAAAGGTGAA GCTTGAAGAT ATCCGGCCGG
B.s. ywtD   ACAGCAGTGG GCAGTGGGCG AGAAGGTAGC CCCTCAGAAC ATAAAGCCTG 701                                              750
B.l. ywtD   GTGATGTTTT GTTTTTCAGC AATACGTACA AACCGGGAAT ATCCCATAAC
B.s. ywtD   GTGATGTCGT CTATTTCAGC AATACGTATA AAACGGGAAT TTCACATGCA 751                                              800
B.l. ywtD   GGCATCTATG CCGGGGGCGG GCGGTTTATC CATGCGAGCC GTTCAAATAA
B.s. ywtD   GGCATTTATG CGGGCGCAGG CAGGTTCATT CAGGCAAGCC GGTCAGAAAA 801                                              850
B.l. ywtD   AGTGACGATA TCCTACTTGT CGGCTTCCTA TTGGCAGAAG AAGTTCACAG
B.s. ywtD   AGTAACCATT TCCTATTTGT CAGAGGATTA CTGGAAATCG AAGATGACGG 851                                              900
B.l. ywtD   GAGTCAGACG TTTTGACAAC ATGTCCCTGC CAAAA...AA TCCGATTGTA
B.s. ywtD   GTATTCGCCG ATTTGACAAC CTGACAATCC GAAAGAAAA TCCGATTGTT 901                                              950
B.l. ywtD   TCCGAAGCCA TCAGGCATAT CGGCGAAGTC GGTTATCAAA AAGGCGGCAC
B.s. ywtD   TCCGAAGCGA CGCTTTATGT CGGAGAAGTG CCTTACAAAC AGGGCGGAGT 951                                             1000
B.l. ywtD   ATCGCCTAAA GAAGGCTTTG ATACGGCTGG GTTTATCCAA TATGTCTACA
B.s. ywtD   AACACCTGAG ACGGGATTTG ATACAGCTGG ATTTGTCCAA TATGTATACC 1001                                            1050
B.l. ywtD   AAACGGCGGC AGGAGTGGAG CTTCCGAGGT ATGCTGACAA ACAATACAGC
B.s. ywtD   AGAAAGCAGC CGGTATTTCC CTGCCTCGAT ACGCAACAAG CCAGTACAAT 1051                                            1100
B.l. ywtD   ACGGGTAAGA AAATTACCAA ACAGGAGCTT GAGCCTGGAG ACATCGTCTT
B.s. ywtD   GCCGGAACTA AGATTGAGAA GGCGGACCTG AAGCCGGGAG ACATTGTGTT 1101                                            1150
B.l. ywtD   CTTTAAAGGA ACCACTGTTA TGAATCCCGC CATCTATATC GGAAACGGCC
B.s. ywtD   CTTTCAATCA ACAA..GCT. TAAATCCCTC CATCTATATC GGAAACGGAC 1151                                            1200
B.l. ywtD   AGGTCGTTCT TGTCACCTTG TCTGCCGGTG TAACGACAGC AGATATGGAG
B.s. ywtD   AAGTTGTTCA TGTCACATTA TCAAACGGCG TGACCATTAC CAATATGAAC 1201                                            1250
B.l. ywtD   ACGAGCGCCT ATTGGAAAGA TAAATACGCC GGAAGCGTCA GAATTGAGTA
B.s. ywtD   ACGAGCACAT ATTGGAAGGA TAAATACGCA GGAAGTATAC GGGTGCAA..

1251
B.l. ywtD   G
B.s. ywtD
```

Figure 6

```
              1                                                      50
B.l. YwsC    MNEFTYQIPR RRCRQTMWVM LLACVIVVGI GIYEKRRHQQ NIDALPVRVN
B.s. YwsC    .......... ......MWLL IIACAVILVI GILEKRRHQK NIDALPVRVN 51                                                     100
B.l. YwsC    INGIRGKSTV TRLTTGILIE AGYKTVGKTT GTDARMIYWD TPEEKPIKRK
B.s. YwsC    INGIRGKSTV TRLTTGILIE AGYKTVGKTT GTDARMIYWD TPEEKPIKRK 101                                                    150
B.l. YwsC    PQGPNIGEQK EVMKETVERG ANAIVSECMA VNPDYQIIFQ EELLQANIGV
B.s. YwsC    PQGPNIGEQK EVMRETVERG ANAIVSECMA VNPDYQIIFQ EELLQANIGV 151                                                    200
B.l. YwsC    IVNVLEDHMD VMGPTLDEIA EAFTATIPYN GHLVITDSEY TDFFKQIAKE
B.s. YwsC    IVNVLEDHMD VMGPTLDEIA EAFTATIPYN GHLVITDSEY TEFFKQKAKE 201                                                    250
B.l. YwsC    RNTKVIVADN SKITDEYLRQ FEYMVFPDNA SLALGVAQAL GIDEETAFKG
B.s. YwsC    RNTKVIIADN SKITDEYLRK FEYMVFPDNA SLALGVAQAL GIDEETAFKG 251                                                    300
B.l. YwsC    MLNAPPDPGA MRILPLMNAK NPGHFVNGFA ANDAASTLNI WKRVKEIGYP
B.s. YwsC    MLNAPPDPGA MRILPLISPS EPGHFVNGFA ANDASSTLNI WKRVKEIGYP 301                                                    350
B.l. YwsC    TDQPIVIMNC RADRVDRTQQ FAEDVLPYIE ASELVLIGET TEPIVKAYEA
B.s. YwsC    TDDPIIIMNC RADRVDRTQQ FANDVLPYIE ASELILIGET TEPIVKAYEE 351                                                    400
B.l. YwsC    GKIPADKLFD FEHKSTEEIM FMLKNKLEGR VIYGVGNIHG AAEPLIEKIQ
B.s. YwsC    GKIPADKLHD LEYKSTDEIM ELLKKSMHNR VIYGVGNIHG AAEPLIEKIH

401
B.l. YwsC    DYKIKQLVS
B.s. YwsC    EYKVKQLVS
```

Figure 7

```
            1                                                              50
B.l. YwsC'  MWVMLLACVI VVGIGIYEKR RHQQNIDALP VRVNINGIRG KSTVTRLTTG
B.s. YwsC   MWLLIIACAV ILVIGILEKR RHQKNIDALP VRVNINGIRG KSTVTRLTTG 51                                                             100
B.l. YwsC'  ILIEAGYKTV GKTTGTDARM IYWDTPEEKP IKRKPQGPNI GEQKEVMKET
B.s. YwsC   ILIEAGYKTV GKTTGTDARM IYWDTPEEKP IKRKPQGPNI GEQKEVMRET 101                                                            150
B.l. YwsC'  VERGANAIVS ECMAVNPDYQ IIFQEELLQA NIGVIVNVLE DHMDVMGPTL
B.s. YwsC   VERGANAIVS ECMAVNPDYQ IIFQEELLQA NIGVIVNVLE DHMDVMGPTL 151                                                            200
B.l. YwsC'  DEIAEAFTAT IPYNGHLVIT DSEYTDFFKQ IAKERNTKVI VADNSKITDE
B.s. YwsC   DEIAEAFTAT IPYNGHLVIT DSEYTEFFKQ KAKERNTKVI IADNSKITDE 201                                                            250
B.l. YwsC'  YLRQFEYMVF PDNASLALGV AQALGIDEET AFKGMLNAPP DPGAMRILPL
B.s. YwsC   YLRKFEYMVF PDNASLALGV AQALGIDEET AFKGMLNAPP DPGAMRILPL 251                                                            300
B.l. YwsC'  MNAKNPGHFV NGFAANDAAS TLNIWKRVKE IGYPTDQPIV IMNCRADRVD
B.s. YwsC   ISPSEPGHFV NGFAANDASS TLNIWKRVKE IGYPTDDPII IMNCRADRVD 301                                                            350
B.l. YwsC'  RTQQFAEDVL PYIEASELVL IGETTEPIVK AYEAGKIPAD KLFDFEHKST
B.s. YwsC   RTQQFANDVL PYIEASELIL IGETTEPIVK AYEEGKIPAD KLHDLEYKST 351                             393
B.l. YwsC'  EEIMFMLKNK LEGRVIYGVG NIHGAAEPLI EKIQDYKIKQ LVS
B.s. YwsC   DEIMELLKKS MHNRVIYGVG NIHGAAEPLI EKIHEYKVKQ LVS
```

Figure 8

```
            1                                                   50
B.l. YwtA   MFGSDLYIAL ILGVLLSLIF AEKTGIVPAG LVVPGYLGLV FNQPIFMLLV
B.s. YwtA   MFGSDLYIAL ILGVLLSLIF AEKTGIVPAG LVVPGYLGLV FNQPVFILLV 51                                                  100
B.l. YwtA   LFVSLLTYVI VKFGLSKIMI LYGRRKFAAM LITGILLKIG FDFIYPVMPF
B.s. YwtA   LLVSLLTYVI VKYGLSKFMI LYGRRKFAAM LITGIVLKIA FDFLYPIVPF 101                                                 149
B.l. YwtA   EIAEFRGIGI IVPGLIANTI QRQGLTITLG STLLLSGATF VIMYAYYLI
B.s. YwtA   EIAEFRGIGI IVPGLIANTI QKQGLTITFG STLLLSGATF AIMFVYYLI
```

Figure 9

```
              1                                                      50
B.l. YwtB    MKKQLNFQEK LLKLTKQEKK KTNKHVFIVL PVIFCLMFVF TWVGSAKTPS
B.s. YwtB    MKKELSFHEK LLKLTKQQKK KTNKHVFIAI PIVFVLMFAF MWAGKAETP.

51                                                    100
B.l. YwtB    QMDKKEDAKL TATFVGDIMM GRNVEKVTNL HGSESVFKNV KPYFNVSDFI
B.s. YwtB    KVKTYSDDVL SASFVGDIMM GRYVEKVTEQ KGADSIFQYV EPIFRASDYV 101                                                   150
B.l. YwtB    TGNFENPVTN AKDYQEAEKN IHLQTNQESV ETLKKLNFSV LNFANNHAMD
B.s. YwtB    AGNFENPVTY QKNYKQADKE IHLQTNKESV KVLKDMNFTV LNSANNHAMD 151                                                   200
B.l. YwtB    YGEDGLKDTL NKFSNENLEL VGAGNNLEDA KQHVSYQNVN GVKIATLGFT
B.s. YwtB    YGVQGMKDTL GEFAKQNLDI VGAGYSLSDA KKKISYQKVN GVTIATLGFT 201                                                   250
B.l. YwtB    DVYTKNFTAK KNRGGVLPLS PKIFIPMIAE ASKKADLVLV HVHWGQEYDN
B.s. YwtB    DVSGKGFAAK KNTPGVLPAD PEIFIPMISE AKKHADIVVV QSHWGQEYDN 251                                                   300
B.l. YwtB    EPNDRQKDLA KAIADAGADV IIGAHPHVLE PIEVYNGTVI FYSLGNFVFD
B.s. YwtB    DPNDRQRQLA RAMSDAGADI IVGHHPHVLE PIEVYNGTVI FYSLGNFVFD 301                                                   350
B.l. YwtB    QGWSRTRDSA LVQYHLMNDG KGRFEVTPLN IREATPTPLG KSDFLKRKAI
B.s. YwtB    QGWTRTRDSA LVQYHLKKNG TGRFEVTPID IHEATPAPV. KKDSLKQKTI 351                          389
B.l. YwtB    FRQLTKGTNL DWKEENGKLT FEVDHADKLK NNKNGVVNK
B.s. YwtB    IRELTKDSNF AWKVEDGKLT FDIDHSDKLK SK.......
```

Figure 10

```
              1                                                        50
B.l. ywtD   MIKKAANKKL VLFCGIAVLW MSLFLUNHND VRADUIGEKI AEUARQLEGA
B.s. ywtD   .MNTLANWKK FLLVAVIICF LVPIMTKAEI AEADTSSELI VSEAKNLLGY 51                                                       100
B.l. ywtD   KYSYGGEKPK UGFDSSGFVQ YVFQSLDIUL PRUVKEQSUL GSSVGRQQLE
B.s. ywtD   QYKYGGETPK EGFDPSGLIQ YVFSKADIHL PRSVNDQYKI GTAVKPENLK 101                                                      150
B.l. ywtD   KGDLVFFKNA ELESDGPUHV AIYLGNDQII HSUKSNGVVV UKLEGSSYWS
B.s. ywtD   PGDILFFKKE GSTGTVPTHD ALYIGDGQMV HSTQSKGVII TNYKKSSYWS 151                                                      200
B.l. ywtD   SGYFKAKRIU KEPEISMDPV VQKAKSYVGV PYVFGGNSPD LGFDCSGLUQ
B.s. ywtD   GTYIGARRIA ADPATADVPV VQEAEKYIGV PYVFGGSTPS EGFDCSGLVQ 201                                                      250
B.l. ywtD   YVFREVLGVY LPRSAEQQWA VGQKVKLEDI RPGDVLFFSN UYKPGISHNG
B.s. ywtD   YVFQQALGIY LPRSAEQQWA VGEKVAPQNI KPGDVVYFSN TYKTGISHAG 251                                                      300
B.l. ywtD   IYAGGGRFIH ASRSNKVUIS YLSASYWQKK FUGVRRFDNM SLPK.NPIVS
B.s. ywtD   IYAGAGRFIQ ASRSEKVTIS YLSEDYWKSK MTGIRRFDNL TIPKENPIVS 301                                                      350
B.l. ywtD   EAIRHIGEVG YQKGGUSPKE GFDUAGFIQY VYKUAAGVEL PRYADKQYSU
B.s. ywtD   EATLYVGEVP YKQGGVTPET GFDTAGFVQY VYQKAAGISL PRYATSQYNA 351                                                      400
B.l. ywtD   GKKIUKQELE PGDIVFFKGU UVMNPAIYIG NGQVVLVULS AGVUUADMEU
B.s. ywtD   GTKIEKADLK PGDIVFFQST S.LNPSIYIG NGQVVHVTLS NGVTITNMNT 401        415
B.l. ywtD   SAYWKDKYAG SVRIE
B.s. ywtD   STYWKDKYAG SIRVQ
```

MICROORGANISMS PROVIDING NOVEL GENE PRODUCTS FORMING OR DECOMPOSING POLYAMINO ACIDS

CROSS REFERENCE TO RELATED APPLICATIONS

The present application is a Section 365(c) continuation of International Application No. PCT/EP2005/006289 filed 11 Jun. 2005, which in turn claims the priority of DE Application 10 2004 030 938.8 filed Jun. 26, 2004, each of which is incorporated herein by reference.

FIELD OF THE INVENTION

The present invention relates to five or four novel genes and their gene products from *Bacillus licheniformis* and sufficiently similar genes and proteins which are involved in vivo in the formation, the modification and/or the degradation of polyamino acids, and can be used for this purpose, and, based thereon, improved biotechnological production methods by microorganisms which are characterized by an inactivation or activation of these genes.

BACKGROUND OF THE INVENTION

The present invention is in the area of biotechnology, in particular the preparation of viable products by fermentation of microorganisms able to form the viable products of interest. This includes for example the preparation of low molecular weight compounds, for instance of dietary supplements or pharmaceutically relevant compounds, or of proteins for which, because of their diversity, there is in turn a large area of industrial uses. In the first case, the metabolic properties of the relevant microorganisms are utilized and/or modified to prepare the viable products; in the second case, cells which express the genes of the proteins of interest are employed. Thus in both cases, genetically modified organisms (GMO) are mostly involved.

There is an extensive prior art on the fermentation of microorganisms, especially also on the industrial scale; it extends from the optimization of the relevant strains in relation to the formation rate and the nutrient utilization via the technical design of the fermenters and up to the isolation of the valuable products from the relevant cells themselves and/or the fermentation medium. Both genetic and microbiological, and process engineering and biochemical approaches are applied thereto. The aim of the present invention is to improve this process in relation to a common property of the microorganisms employed, which impairs the actual fermentation step, specifically at the level of the genetic properties of the strains employed.

For industrial biotechnological production, the relevant microorganisms are cultured in fermenters which are configured appropriate for their metabolic properties. During the culturing, they metabolize the substrate offered and, besides the actual product, normally form a large number of other substances in which there is ordinarily no interest and/or which—as explained hereinafter—may lead to difficulties in the fermentation or the working up.

Fermentations are normally very complicated processes in which a large number of different parameters must be adjusted and monitored. Thus, for example, aerobic processes are very often involved, meaning that the microorganisms employed must be supplied adequately with oxygen throughout the fermentation (control of the aeration rate). Further examples of such parameters are the reactor geometry, the continuously changing composition of the nutrient medium, the pH or the $CO_2$ formation rate. A particularly important parameter both in terms of the economics and in relation to the process management per se is the necessary energy input, for example via agitation systems which ensure that the reactor content is mixed as thoroughly as possible. In addition, besides the substrate distribution, also an adequate supply of oxygen to the organisms is ensured.

After completion of the fermentation it is normally necessary, besides the removal of the producer organisms, for the valuable product of interest to be purified and/or concentrated from the so-called fermenter slurry. The working up process can include for example various chromatographic and/or filtration steps. Thus, besides the content of valuable products, also decisive for the success of the overall working up process are the biophysical properties of the fermenter slurry, especially its viscosity immediately after completion of the fermentation.

The properties thereof are also influenced by the metabolic activities of the chosen microorganisms, it also being possible for unwanted effects to occur. These include for example a frequent increase in the viscosity of the nutrient medium during the fermentation. This impairs the mixing and thus the transport of matter and the oxygen supply inside the reactor. Additional difficulties mostly arise during the subsequent working up because increased viscosities considerably impair for example the efficiency of filtration processes.

It is known in particular that species of the genus *Bacillus* produce slime which consists essentially of poly-gamma-glutamate (PGA) and/or -aspartate, meaning polyamino acids linked via the relevant gamma peptide bonds. In scientific studies on *Bacillus subtilis* it is mainly the three genes ywsC, ywtA and ywtB and the gene products derived therefrom which are connected with the production of poly-gamma-glutamate; the gene product of ywtD is involved in the degradation. The general designation "ywt" for genes is in this connection synonymous with the abbreviations "cap" and "pgs" which are in common use for the same functions. This is explained below.

The publication "Physiological and biochemical characteristics of poly gamma-glutamate synthetase complex of *Bacillus subtilis*" (2001) by M. Ashiuchi et al., in *Eur. J. Biochem.*, volume 268, pages 5321-5328, describes the PgsBCA (poly-gamma-glutamate synthetase complex BCA) enzyme complex, which consists of the three subunits PgsB, PgsC and PgsA, from *B. subtilis*. This complex is, according to this, an atypical amide ligase which converts both the D and the L enantiomer of glutamate into the corresponding polymer. According to this publication, a gene disruption experiment described therein is to be regarded as proof that this complex is the only one catalyzing this reaction in *B. subtilis*.

Y. Urushibata et al. demonstrate in the publication "Characterization of the *Bacillus subtilis* ywsC gene, involved in gamma-polyglutamic acid production" (2002), in *J. Bacteriol.*, volume 184, pages 337-343, inter alia via deletion mutations in the three genes ywsC, ywtA and ywtB, that the three gene products responsible in *B. subtilis* for the formation of PGA are encoded by these three genes. They form in this sequence and together with the subsequent gene ywtC a coherent operon in this microorganism.

The fact that a further gene relevant for the metabolism of PGA is located in the genome of *B. subtilis* downstream from ywtC in its own operon is shown by T. Suzuki and Y. Tahara in the publication "Characterization of the *Bacillus subtilis* ywtD gene, whose product is involved in gamma-polyglutamic acid degradation" (2003), *J. Bacteriol.*, volume 185, pages 2379-2382. This gene codes for a DL-endopeptidase which is able to hydrolyze PGA and thus can be referred to as gamma-DL-glutamyl hydrolase.

An up-to-date survey of these enzymes is additionally provided by the article "Biochemistry and molecular genetics of poly-gamma-glutamate synthesis" by M. Ashiuchi and H. Misono in Appl. *Microbiol. Biotechnol.*, volume 59, pages 9-14 of 2002. The genes homologous to pgsB, pgsC and pgsA and coding for the PGA synthase complex in *B. anthracis* are referred to therein as capB, capC and capA. The gene located downstream is referred to according to this article as dep (for "D-PGA depolymerase") in *B. anthracis* and as pgdS (for "PGA depolymerase") in *B. subtilis*.

In the current state of the art, these enzymic activities are already in positive use mainly for preparing poly-gamma-glutamate as raw material, for example for use in cosmetics, although their exact DNA sequences and amino acid sequences have not to date been known—especially from *B. licheniformis*. Thus, for example, the application JP 08308590 A discloses the preparation of PGA by fermentation of the PGA-producing strains itself, namely of *Bacillus* species such as *B. subtilis* and *B. licheniformis*; the isolation of this raw material from the culture medium is also described therein. *B. subtilis* var. chunkookjang represents, according to the application WO 02/055671 A1, a microorganism which is particularly suitable therefor.

Thus, in some fermentations there is an interest in GLA as the valuable product to be produced by the fermentation.

However, the interest in all other fermentations is to prepare other valuable products; in this connection, the formation of polyamino acids means, for the reasons stated above, a negative side effect. A typical procedure for mastering the increased viscosity of the fermentation medium attributable to the formation thereof is to increase the agitator speed. However, this has an effect on the energy input. In addition, the fermented microorganisms are exposed thereby to increasing shear forces representing a considerable stress factor for them. In the end, very high viscosities cannot be overcome even thereby, so that premature termination of the fermentation may be necessary, although production could otherwise be continued.

Slime formation, as a negative side effect of numerous fermentation processes, may thus have negative effects on the overall result of fermentation for diverse reasons. Conventional methods for successfully continuing fermentations in progress despite an increasing viscosity of the nutrient medium can be designated only as inadequate, especially because they do not represent a causal control.

SUMMARY OF THE INVENTION

The more pressing problem was thus to suppress as far as possible an unwanted formation of slime, especially a slime attributable to poly-gamma-amino acids such as poly-gamma-glutamate, during the fermentation of microorganisms. It was intended in particular to find a solution representing a causal control. A further aspect of this problem is the provision of the relevant genes for a positive utilization of the GLA-synthesizing gene products and for the degradation and/or modification thereof.

Each of the following proteins involved in the formation or degradation of polyamino acids represents in each case a partial solution of in principle equal value for this problem:

YwsC (CapB, PgsB) which is encoded by a nucleotide sequence ywsC which shows at least 80% identity to the nucleotide sequence indicated in SEQ ID NO. 1;

YwsC' (as truncated variant of YwsC) which is encoded by a nucleotide sequence ywsC' which shows at least 83% identity to the nucleotide sequence indicated in SEQ ID NO. 3;

YwtA (CapC, PgsC) which is encoded by a nucleotide sequence ywtA which shows at least 82% identity to the nucleotide sequence indicated in SEQ ID NO. 5;

YwtB (CapA, PgdA) which is encoded by a nucleotide sequence ywtB which shows at least 72% identity to the nucleotide sequence indicated in SEQ ID NO. 7; and YwtD (Dep, PgdS) which is encoded by a nucleotide sequence ywtD which shows at least 67% identity to the nucleotide sequence indicated in SEQ ID NO. 9.

As is evident for example from the mentioned publication by Urushibata et al., the four or three genes involved in GLA formation are present in *B. subtilis* in succession on the same operon. ywtD is located there directly downstream. It is to be expected that this organization of these components acting together in vivo in a complex, and of the downstream component acting on the polyamino acid formed thereby will also be found in many further microorganisms, in particular of the genus *Bacillus*. Thus, besides the common biochemical function, there also exists at the genetic level an aspect producing unity of the invention.

Further partial solutions are represented by the relevant nucleic acids ywsC, ywsC', ywtA, ywtB and ywtD and, based thereon, the use of relevant nucleic acids for reducing the formation of slime attributable to polyamino acids during the fermentation of the microorganism, and corresponding methods for fermentation of microorganisms. In the reduction according to the invention of the formation of slime at the genetic level, at least one of the genes ywsC, ywsC', ywtA or ywtB is functionally inactivated and/or the activity of ywtD is enhanced. In addition, there is the positive use of these genes or of the derived gene products for the preparation, modification or degradation of poly-gamma-glutamate.

This invention which is applicable in principle to all fermentable microorganisms, especially to those of the genus *Bacillus*, leads to the microorganisms employed for the fermentative production of valuable products other than polyamino acids, in particular of pharmaceutically relevant low molecular weight compounds or of proteins, being prevented at the genetic level from forming polyamino acids, especially GLA, or immediately degrading them again. On the one hand, this has an advantageous effect on the viscosity of the culture medium and additionally on the mixability, the oxygen input and the energy to be expended, and on the other hand the working up of the product of interest is considerably facilitated. In addition, most of the raw materials employed, for instance the N source, is not converted into a product of no interest, so that overall a higher fermentation yield is to be expected.

According to a further aspect of this invention, said genes are now available for a positive use of the GLA-synthesizing gene products or for their degradation and/or modification, specifically by the derived proteins YwsC, YwsC', YwtA, YwtB and/or YwtD being produced biotechnologically and being introduced in the cells producing them or independently thereof as catalysts into appropriate reaction mixtures.

BRIEF DESCRIPTION OF THE FIGURES

FIG. 1: Alignment of the gene ywsC (SEQ ID NO. 1) from *B. licheniformis* DSM 13 (B.l. ywsC) with the homologous gene ywsC (SEQ ID NO. 11) from *B. subtilis* (B.s. ywsC).

FIG. 2: Alignment of the gene ywsC' (SEQ ID NO. 3) from *B. licheniformis* DSM 13 (B.l. ywsC') with the homologous gene ywsC (SEQ ID NO. 11) from *B. subtilis* (B.s. ywsC).

FIG. 3: Alignment of the gene ywtA (SEQ ID NO. 5) from *B. licheniformis* DSM 13 (B.l. ywtA) with the homologous gene ywtA (SEQ ID NO. 13) from *B. subtilis* (B.s. ywtA).

FIG. 4: Alignment of the gene ywtB (SEQ ID NO. 7) from *B. licheniformis* DSM 13 (B.l. ywtB) with the homologous gene ywtB (SEQ ID NO. 15) from *B. subtilis* (B.s. ywtB).

FIG. 5: Alignment of the gene ywtD (SEQ ID NO. 9) from *B. licheniformis* DSM 13 (B.l. ywtD) with the homologous gene ywtD (SEQ ID NO. 17) from *B. subtilis* (B.s. ywtD).

FIG. 6: Alignment of the protein YwsC (SEQ ID NO. 2) from *B. licheniformis* DSM 13 (B.l. YwsC) with the homologous protein YwsC (SEQ ID NO. 12) from *B. subtilis* (B.s. YwsC).

FIG. 7: Alignment of the protein YwsC' (SEQ ID NO. 4) from *B. licheniformis* DSM 13 (B.l. YwsC') with the homologous protein YwsC (SEQ ID NO. 12) from *B. subtilis* (B.s. YwsC).

FIG. 8: Alignment of the protein YwtA (SEQ ID NO. 6) from *B. licheniformis* DSM 13 (B.l. YwtA) with the homologous protein YwtA (SEQ ID NO. 14) from *B. subtilis* (B.s. YwtA).

FIG. 9: Alignment of the protein YwtB (SEQ ID NO. 8) from *B. licheniformis* DSM 13 (B.l. YwtB) with the homologous protein YwtB (SEQ ID NO. 16) from *B. subtilis* (B.s. YwtB).

FIG. 10: Alignment of the protein YwtD (SEQ ID NO. 10) from *B. licheniformis* DSM 13 (B.l. YwtD) with the homologous protein YwtD (SEQ ID NO. 18) from *B. subtilis* (B.s. YwtD).

DETAILED DESCRIPTION OF THE INVENTION

The first partial solution represents a protein YwsC (CapB, PgsB) which is involved in the formation of polyamino acids and which is encoded by a nucleotide sequence ywsC which shows at least 80% identity to the nucleotide sequence indicated in SEQ ID NO. 1.

This specific enzyme was obtained by analysis of the genome of *B. licheniformis* DSM 13 (see Example 1). This protein is made reproducibly available through the nucleotide and amino acid sequences indicated in SEQ ID NO. 1 and 2 of the present application (see Example 1).

This takes the form, in agreement with the literature information mentioned in the introduction, of a subunit of the poly-gamma-glutamate synthetase complex. The protein known in the state of the art and most similar thereto has been found to be the homolog YwsC from *B. subtilis* which is noted in the GenBank database (National Center for Biotechnology Information NCBI, National Institutes of Health, Bethesda, Md., USA) under the accession number AB046355.1 and has a homology of 75.4% identity at the nucleic acid level, while the agreement is 86.1% identity at the amino acid level (see Example 2). These significant agreements suggest not only the same biochemical function, but also the presence within the claimed range of a large number of related proteins having the same function which is likewise included in the protection conferred by the present application.

The following embodiments are to be allocated to this first partial solution:

Any corresponding protein YwsC which is encoded by a nucleotide sequence which shows with increasing preference at least 85%, 90%, 92%, 94%, 96%, 97%, 98%, 99% and particularly preferably 100% identity to the nucleotide sequence indicated in SEQ ID NO. 1. This is because the conclusion to be drawn from an increase in agreement of the sequence is that there is an increase in agreement in the function and mutual replaceability at the genetic level.

Any protein YwsC (CapB, PgsB) involved in the formation of polyamino acids and having an amino acid sequence which shows at least 91% identity, with increasing preference at least 92%, 93%, 94%, 95%, 96%, 97%, 98%, 99% and particularly preferably 100% identity to the amino acid sequence indicated in SEQ ID NO. 2.

In connection with the present application, an expression of the form "at least X %" means "X % to 100%, including the extreme values X and 100 and all integral and non-integral percentages between them".

The specific protein obtained from *B. licheniformis* DSM13 is most preferred in each case, because this is specifically described in the present application and is made available 100% reproducibly.

The second partial solution represents a protein YwsC' (as truncated variant of YwsC) which is involved in the formation of polyamino acids and is encoded by a nucleotide sequence ywsC', which shows at least 83% identity to the nucleotide sequence indicated in SEQ ID NO. 3.

This specific enzyme was obtained by analysis of the genome of *B. licheniformis* DSM 13 (see Example 1). This protein is made reproducibly available through the nucleotide and amino acid sequences indicated in SEQ ID NO. 3 and 4 in the present application (see Example 1).

As additionally explained in Example 1, the comparison, shown in FIG. 6, of the sequences between YwsC from *B. licheniformis* and *B. subtilis* suggests that the first 16 amino acids of YwsC from *B. licheniformis* are immaterial for its function as subunit C of the poly-gamma-glutamate synthetase complex. The present invention is thus also implemented with this truncated variant.

Mentioned in connection with the present application of "five or four genes" means that ywsC and ywsC' are treated according to the invention as two genes and the derived proteins are treated as two proteins. On the other hand, it is probably to be assumed that both these "genes" are not in each case present in vivo in the relevant organisms, but in each case only one thereof, so that only one corresponding gene product YwsC or YwsC' is also likely to be present. Thus, the first and the second partial solution represent to a certain extent two aspects of the same subject matter. Separation into two partial solutions does, however, appear justified because of the differences at the amino acid level.

The protein known in the state of the art and most similar thereto has again been found to be the homolog YwsC from *B. subtilis* which is noted in the GenBank database under the accession number AB046355.1 and has a homology of 78.5% identity at the nucleic acid level; the agreement at the amino acid level is 89.6% identity (see Example 2).

In accordance with the statements above, the following embodiments are to be allocated to this second partial solution:

Any corresponding protein YwsC' which is encoded by a nucleotide sequence which shows with increasing preference at least 85%, 90%, 92%, 94%, 96%, 97%, 98%, 99% and particularly preferably 100% identity to the nucleotide sequence indicated in SEQ ID NO. 3.

Any protein YwsC' (as truncated variant of YwsC) which is involved in the formation of polyamino acids and has an amino acid sequence which shows at least 94% identity, with increasing preference at least 95%, 96%, 97%, 98%, 99% and particularly preferably 100% identity to the amino acid sequence indicated in SEQ ID NO. 4.

The specific protein obtained from *B. licheniformis* DSM13 is most preferred in each case because this is specifically described in the present application and is made available 100% reproducibility.

The third partial solution represents a protein YwtA (CapC, PgsC) which is involved in the formation of polyamino acids and which is encoded by a nucleotide sequence ywtA which shows at least 82% identity to the nucleotide sequence indicated in SEQ ID NO. 5.

This specific enzyme was obtained by analysis of the genome of *B. licheniformis* DSM13 (see Example 1). This protein is made reproducibly available through the nucleotide and amino acid sequences indicated in SEQ ID NO. 5 and 6 in the present application (see Example 1).

This takes the form, in agreement with the literature information mentioned in the introduction, of a further subunit of the poly-gamma-glutamate synthetase complex. The protein known in the state of the art and most similar thereto has been found to be the homolog YwsA from *B. subtilis* which is noted in the GenBank database under the accession number AB046355.1 and has a homology of 77.8% identity at the nucleic acid level, while the agreement is 89.9% identity at the amino acid level (see Example 2). These significant agreements suggest not only the same biochemical function, but also the presence within the claimed range of a large number of related proteins having the same function which is likewise included in the protection conferred by the present application.

The following embodiments are to be allocated to this third partial solution:

Any corresponding protein YwtA which is encoded by a nucleotide sequence which shows with increasing preference at least 85%, 90%, 92%, 94%, 96%, 97%, 98%, 99% and particularly preferably 100% identity to the nucleotide sequence indicated in SEQ ID NO. 5.

Any protein YwtA (CapC, PgsC) involved in the formation of polyamino acids and having an amino acid sequence which shows at least 94% identity, with increasing preference at least 95%, 96%, 97%, 98%, 99% and particularly preferably 100% identity to the amino acid sequence indicated in SEQ ID NO. 6.

The specific protein obtained from *B. licheniformis* DSM13 is most preferred in each case, because this is specifically described in the present application and is made available 100% reproducibly.

The fourth partial solution represents a protein YwtB (CapA, PgsA) which is involved in the formation of polyamino acids and is encoded by a nucleotide sequence ywtB, which shows at least 72% identity to the nucleotide sequence indicated in SEQ ID NO. 7.

This specific enzyme was obtained by analysis of the genome of *B. licheniformis* DSM 13 (see Example 1). This protein is made reproducibly available through the nucleotide and amino acid sequences indicated in SEQ ID NO. 7 and 8 in the present application (see Example 1).

This takes the form, in agreement with the literature information mentioned in the introduction, of the third subunit of the poly-gamma-glutamate synthetase complex. The protein known in the state of the art and most similar thereto has been found to be the homolog YwsA from *B. subtilis* which is noted in the GenBank database under the accession number AB046355.1 and has a homology of 67.1% identity at the nucleic acid level, while the agreement is 65.8% identity at the amino acid level (see Example 2). These significant agreements suggest not only the same biochemical functional but also the presence within the claimed range of a large number of related proteins having the same function which is likewise included in the protection conferred by the present application.

The following embodiments are to be allocated to this fourth partial solution:

Any corresponding protein YwtB which is encoded by a nucleotide sequence which shows with increasing preference at least 75%, 80%, 85%, 90%, 92%, 94%, 96%, 97%, 98%, 99% and particularly preferably 100% identity to the nucleotide sequence indicated in SEQ ID NO. 7.

Any protein YwtB (CapA, PgsA) involved in the formation of polyamino acids and having an amino acid sequence which shows at least 70% identity, with increasing preference at least 75%, 80%, 90%, 95%, 96%, 97%, 98%, 99% and particularly preferably 100% identity to the amino acid sequence indicated in SEQ ID NO. 8.

The specific protein obtained from *B. licheniformis* DSM13 is most preferred in each case, because this is specifically described in the present application and is made available 100% reproducibly.

The fifth partial solution represents a protein YwtD (Dep, PgdS) which is involved in the degradation of polyamino acids and is encoded by a nucleotide sequence ywtD, which shows at least 67% identity to the nucleotide sequence indicated in SEQ ID NO. 9.

This specific enzyme was obtained by analysis of the genome of *B. licheniformis* DSM 13 (see Example 1). This protein is made reproducibly available through the nucleotide and amino acid sequences indicated in SEQ ID NO. 9 and 10 in the present application (see Example 1).

This takes the form, in agreement with the literature information mentioned in the introduction, of the gamma-DL-glutamyl hydrolase, D-PGA depolymerase or PGA depolymerase. The protein known in the state of the art and most similar thereto was found to be the homolog YwtD from *B. subtilis* which is noted in the GenBank database under the accession number AB080748 and has a homology of 62.3% identity at the nucleic acid level; the agreement at the amino acid level is 57.3% identity (see Example 2). These significant agreements suggest not only the same biochemical function, but also the presence within the claimed range of a large number of related proteins having the same function which is likewise included in the protection conferred by the present application.

The following embodiments are to be allocated to this fifth partial solution:

Any corresponding protein YwtD which is encoded by a nucleotide sequence which shows with increasing preference at least 70%, 75%, 80%, 85%, 90%, 92%, 94%, 96%, 97%, 98%, 99% and particularly preferably 100% identity to the nucleotide sequence indicated in SEQ ID NO. 9.

Any protein YwtD (Dep, PgdS) involved in the degradation of polyamino acids and having an amino acid sequence which shows at least 62% identity, with increasing preference at least 65%, 70%, 75%, 80%, 90%, 95%, 96%, 97%, 98%, 99% and particularly preferably 100% identity to the amino acid sequence indicated in SEQ ID NO. 10.

The specific protein obtained from *B. licheniformis* DSM13 is most preferred in each case, because this is specifically described in the present application and is made available 100% reproducibly.

Preference is given in each case among these in each case to a previously described protein of the invention which is involved in the formation or degradation of polyamino acids and which is naturally produced by a microorganism, preferably by a bacterium, particularly preferably by a Gram-positive bacterium, preferably among these by one of the genus *Bacillus*, particularly preferably among these by one of the species *B. licheniformis* and very particularly preferably among these by *B. licheniformis* DSM13.

This is because, in accordance with the problem, there was interest in improving the fermentation of microorganisms, for which bacteria from among these particularly Gram-positive ones, are frequently used, especially those which, like *Bacillus*, are able to secrete produced valuable products and proteins. In addition, there is a wealth of clinical experience concerning this. In addition, it was possible to detect, as mentioned, the proteins indicated in the sequence listing for *B. licheniformis*, specifically *B. licheniformis* DSM13. It is to be expected that an increasing degree of relationship of the relevant organisms will be associated with an increasing extent of agreement of the nucleotide and amino acid sequences and thus their exchangeability.

In accordance with that stated hitherto, the following in each case relevant nucleic acids are to be allocated as further expressions of the present invention to the stated partial solutions:

Nucleic acid ywsC (capB, pgsB) which codes for a gene product involved in the formation of polyamino acids and has a nucleotide sequence which shows at least 80% identity to the nucleotide sequence indicated in SEQ ID NO. 1;

a corresponding nucleic acid ywsC having a nucleotide sequence which shows with increasing preference at least 85%, 90%, 92%, 94%, 96%, 97%, 98%, 99% and particularly preferably 100% identity to the nucleotide sequence indicated in SEQ ID NO. 1;

nucleic acid ywsC' (as truncated variant of ywsC) which codes for a gene product involved in the formation of polyamino acids and has a nucleotide sequence which shows at least 83% identity to the nucleotide sequence indicated in SEQ ID NO. 3;

a corresponding nucleic acid ywsC' having a nucleotide sequence which shows with increasing preference at least 85%, 90%, 92%, 94%, 96%, 97%, 98%, 99% and particularly preferably 100% identity to the nucleotide sequence indicated in SEQ ID NO. 3;

nucleic acid ywtA (capC, pgsC) which codes for a gene product involved in the formation of polyamino acids and has a nucleotide sequence which shows at least 82% identity to the nucleotide sequence indicated in SEQ ID NO. 5;

a corresponding nucleic acid ywtA having a nucleotide sequence which shows with increasing preference at least 85%, 90%, 92%, 94%, 96%, 97%, 98%, 99% and particularly preferably 100% identity to the nucleotide sequence indicated in SEQ ID NO. 5;

nucleic acid ywtB (capA, pgsA), which codes for a gene product involved in the formation of polyamino acids and has a nucleotide sequence which shows at least 72% identity to the nucleotide sequence indicated in SEQ ID NO. 7;

a corresponding nucleic acid ywtB having a nucleotide sequence which shows with increasing preference at least 75%, 80%, 85%, 90%, 92%, 94%, 96%, 97%, 98%, 99% and particularly preferably 100% identity to the nucleotide sequence indicated in SEQ ID NO. 7;

nucleic acid ywtD (dep, pgdS) which codes for a gene product involved in the degradation of polyamino acids and has a nucleotide sequence which shows at least 67% identity to the nucleotide sequence indicated in SEQ ID NO. 9; and a corresponding nucleic acid ywtD having a nucleotide sequence which shows with increasing preference at least 70%, 75%, 80%, 85%, 90%, 92%, 94%, 96%, 97%, 98%, 99% and particularly preferably 100% identity to the nucleotide sequence indicated in SEQ ID NO. 9.

The nucleic acids provided herewith can be employed by methods of molecular biology known per se for inactivating or enhancing the activity of the relevant proteins. Thus, inactivations are possible for example via appropriate deletion vectors (see below); enhancement of the activity advantageously takes place by an overexpression which can be achieved with the aid of an expression vector (see below). Thus, the problem posed is implemented via these nucleic acids through inactivation of ywsC, ywsC', ywtA and/or ywtB and/or by enhanced ywtD gene activity.

The corresponding genes falling within the homology ranges indicated in each case can be obtained from the organisms of interest for example with the aid of probes which can be prepared on the basis of sequences 1, 3, 5, 7, or 9. These complete genes may also serve as model for generating PCR primers via which the relevant genes can be rendered accessible from corresponding total DNA preparations; these genes in turn provide the proteins described previously. The success rate in this connection usually increases with the closeness of the relationship of the relevant strain to that which has served to construct the probe or the PCR primers, and thus in the present case to *B. licheniformis*.

Preference is given in each case among these in each case to a nucleic acid of the invention which is naturally present in a microorganism, preferably a bacterium, particularly preferably a Gram-positive bacterium, and among these preferably one of the genus *Bacillus*, particularly preferably among these one of the species *B. licheniformis* and very particularly preferably among these *B. licheniformis* DSM13.

This is because, as stated above, there is a particular interest in utilizing these genes for fermentations of such microorganisms. On the other hand, the present invention is also linked to the possibility of adjusting, via the genes and/or proteins described herein, the metabolism of the polyamino acids, especially gamma-glutamic acid, at least in parts when they are to be synthesized, modified and/or degraded. The success rate for this generally, especially in appropriate transgenic host cells, increases with the degree of agreement of the relevant genes with those of the natural cells.

It is additionally possible to isolate alternative embodiments of the genes and proteins easily from in principle all natural organisms.

A further embodiment of the present invention represents all nucleic acids which code for a protein of the invention described above.

Thus, differences exist, particularly between remotely related species, in the usage of synonymous codons coding for the respective amino acids, with which the protein biosynthesis apparatus also conforms, for instance via the available number of appropriate loaded tRNAs. Transfer of one of said genes into a less related species can be used particularly successfully for example for deletion mutation or for synthesis of the relevant protein if it is appropriately optimized in terms of the codons. It is possible thereby to introduce increasing percentage differences at the DNA level which, however, have no consequence at the amino acid level. For this reason, such nucleic acids also represent implementations of the present invention.

The invention further relates to vectors which comprise a previously designated nucleic acid region of the invention.

This is because in order to handle the nucleic acids relevant to the invention, and thus in particular to prepare for the production of proteins of the invention, they are suitably ligated into vectors. Such vectors and the relevant working methods are described in detail in the prior art. Vectors are commercially available in large number and range of variation, both for cloning and for expression. These include for example vectors derived from bacterial plasmids, from bacteriophages or from viruses, or predominantly synthetic vectors. They are also distinguished according to the nature of the cell types in which they are able to establish themselves, for example into vectors for Gram-negative, for Gram-positive bacteria, for yeasts or for higher eukaryotes. They form suitable starting points for example for molecular biological and biochemical investigations and for the expression of the relevant gene or associated protein. They are virtually indispensable—as is evident from the prior art relevant thereto—in particular for the preparation of constructs for deletion or enhancement of expression.

Vectors preferred among these are those comprising two or more of the nucleic acids of the invention described above.

This is because in addition on the one hand the relevant genes can at the same time be stored or can be expressed under the control of the same promoter. According to another application, a vector which simultaneously comprises two or more intact copies of the genes of the invention can serve to keep alive (rescue) a deletion mutant which is simultaneously deleted in a plurality of these genes. Targeted removal of this vector then results in this plurality of genes being simultaneously switched off.

In another embodiment, the vectors of the invention are cloning vectors.

This is because cloning vectors are, besides the storage, the biological amplification or the selection of the gene of interest, suitable for its molecular biological characterization. At the same time, they represent transportable and storable forms of the claimed nucleic acids and are also starting points for molecular biological techniques which are not linked to cells, such as, for example, PCR or in vitro mutagenesis methods.

The vectors of the invention are preferably expression vectors.

This is because such expression vectors are the basis for implementing the corresponding nucleic acids in biological production systems and thus producing the relevant proteins. Preferred embodiments of this subject matter of the invention are expression vectors which are by genetic elements necessary for expression, for example the natural promoter originally located in front of this gene, or a promoter from a different organism. These elements may be disposed for example in the form of a so-called expression cassette. An alternative possibility is for one or all regulatory elements also to be provided by the respective host cell. Expression vectors are particularly preferred in relation to further properties such as, for example, the optimum copy number matched to the chosen expression system, especially the host cell (see below).

The possibility of forming intact gene products on the basis of a vector existing as a replicon is particularly important for the rescue described above and the switching off of particular genes. Conversely, the provision of an expression vector is the best possibility for enhanced formation of a protein of the invention and thus an increase in the relevant activity.

Cells which, after genetic modification, comprise one of the nucleic acids of the invention designated above form a separate subject matter of the invention.

This is because these cells comprise the genetic information for synthesizing a protein of the invention. By these are meant in particular cells which have been provided with the nucleic acids of the invention by methods known per se, or which are derived from such cells. The host cells suitably selected for this purpose are those which can be cultured relatively simply and/or provide high product yields.

It is necessary in principle in countries where human embryonic stem cells may not be placed under patent protection for such human embryonic stem cells of the invention to be excluded from the protection conferred.

Cells of the invention make it possible for example to amplify the corresponding genes, but also for them to be mutagenized or transcribed and translated and eventually for the relevant proteins to be produced biotechnologically. This genetic information may be present either extrachromosomally as separate genetic element, meaning located in plasmids in the case of bacteria, or be integrated into a chromosome. The choice of a suitable system depends on questions such as, for example, the nature and duration of the storage of the gene or of the organism or the nature of the mutagenesis or selection.

These include, besides the cells which overexpress in particular YwtD, in particular those which comprise one of the genes ywsC, ywsC', ywtA and ywtB via a vector in trans and can thus be used for corresponding deletions (see below).

This explains the preferred embodiment in which said nucleic acid is part of a vector, in particular of a previously described vector, in such a cell.

Host cells which are bacteria are preferred among these.

This is because bacteria are distinguished by short generation times and low demands on the culturing conditions. It is possible thereby to establish cost-effective methods. In addition, there is a wealth of experience in the techniques of fermentation of bacteria. Gram-negative or Gram-positive bacteria may be suitable for a specific production for a wide variety of reasons which are to be ascertained experimentally in the individual case, such as nutrient sources, product formation rate, time required etc.

A preferred embodiment involves a Gram-negative bacterium, in particular one of the genera *Escherichia coli*, *Klebsiella*, *Pseudomonas* or *Xanthomonas*, in particular strains of *E. coli* K12, *E. coli* B or *Klebsiella planticola*, and very especially derivatives of the strain *Escherichia coli* BL21 (DE3), *E. coli* RV308, *E. coli* DH5α, *E. coli* JM109, *E. coli* XL-1 or *Klebsiella planticola* (Rf).

This is because a large number of proteins are secreted into the periplasmic space with Gram-negative bacteria such as, for example, *E. coli*. This may be advantageous for specific applications. The application WO 01/81597 A1 discloses a method which achieves expulsion of the expressed proteins by Gram-negative bacteria too. The Gram-negative bacteria mentioned as preferred are usually available easily, meaning commercially or through public collections of strains, and can be optimized for specific preparation conditions in association with other components such as, for instance, vectors which are likewise available in large number.

An alternative, not less preferred embodiment involves a Gram-positive bacterium, in particular one of the genera *Bacillus*, *Staphylococcus* or *Corynebacterium*, very particularly of the species *Bacillus lentus*, *B. licheniformis*, *B. amyloliquefaciens*, *B. subtilis*, *B. globigii* or *B. alcalophilus*, *Staphylococcus carnosus* or *Corynebacterium glutamicum*, and among these in turn very particularly preferably a derivative of *B. licheniformis* DSM 13.

This is because Gram-positive bacteria have the fundamental difference from Gram-negative ones of immediately releasing secreted proteins into the nutrient medium which surrounds the cells and from which if desired the expressed proteins of the invention can be directly purified from the nutrient medium. In addition, they are related or identical to most of the organisms of origin of industrially important enzymes and mostly themselves produce comparable enzymes, so that they have a similar codon usage and their protein synthesis apparatus is naturally configured appropriately. Derivatives of *B. licheniformis* DSM 13 are very particularly preferred because they on the one hand are likewise widely used as biotechnological producer strains in the state of the art and because on the other hand the present application makes exactly the genes and proteins of the invention from B. licheniformis DSM 13 available, so that implementation of the present invention ought most likely to be successful in such strains.

A further embodiment of the present invention is formed by methods for preparing one or more of the gene products YwsC, YwsC', YwtA, YwtB and YwtD described above.

This includes any method for preparing a protein of the invention described above, for example chemical synthetic methods. However, in relation thereto, all molecular biological, microbiological and biotechnological preparation methods which have been discussed above in individual aspects and are established in the state of the art are preferred. The aim thereof is primarily to obtain the proteins of the invention in order to make them available for appropriate applications, for example for the synthesis, modification or degradation of poly-gamma-glutamate.

Methods preferred in this connection are those taking place with use of a nucleic acid of the invention designated above, preferably taking place with use of a vector of the invention designated above and particularly preferably with use of a cell of the invention designated above.

This is because said nucleic acids, especially the nucleic acids indicated in the sequence listing under SEQ ID NO. 1, 3, 5, 7 and 9, makes the correspondingly preferred genetic information available in microbiologically utilizable form, i.e. for genetic production methods. It is increasingly preferred to provide on a vector which can be utilized particularly successfully by the host cell, or such cells themselves. The relevant production methods are known per se to the skilled worker.

Embodiments of the present invention may on the basis of the relevant nucleic acid sequences also be cell-free expression systems in which the protein biosynthesis is duplicated in vitro. All the elements already mentioned may also be combined to novel methods in order to prepare proteins of the invention. A large number of possible combinations of method steps is conceivable for each protein of the invention moreover, so that optimal methods need to be ascertained experimentally for each specific individual case.

Methods of the invention of such types are further preferred when the nucleotide sequence has been adapted in one or, preferably, more codons to the codon usage of the host strain.

This is because, in accordance with that stated above, transfer of one of said genes into a less related species can be used particularly successfully for synthesizing the relevant protein if it is appropriately optimized in relation to the codon usage.

A further expression of the present invention is the use of a nucleic acid ywsC of the invention described above, of a nucleic acid ywsC' of the invention described above, of a nucleic acid ywtA of the invention described above, of a nucleic acid ywtB of the invention described above or of a corresponding nucleic acid which codes for one of the proteins of the invention described above or in each case parts thereof for the functional inactivation of the respectively relevant gene ywsC, ywsC', ywtA or ywtB in a microorganism.

Functional inactivation means in the context of the present application any type of modification or mutation by which the function of the relevant protein as an enzyme involved in the formation of polyamino acids, or as subunit of such an enzyme, is suppressed. This includes the embodiment where a virtually complete but inactive protein is formed, inactive parts of such a protein are present in the cell, up to the possibilities where the relevant gene is no longer translated or is even completely deleted. Thus, a specific "use" of these factors or genes in this embodiment consists of them no longer acting in their natural manner precisely in the relevant cell. This is achieved according to the subject matter of the invention at the genetic level by switching off the relevant gene.

An alternative embodiment for inactivating the genes ywsC, ywsC', ywtA or ywtB is the use of a nucleic acid ywtD of the invention described above or of a corresponding nucleic acid which codes for one of the proteins of the invention described above for increasing the activity of the relevant gene ywtD in a microorganism.

This is because, as described in the introduction, the in vivo function of this enzyme is to degrade GLA. Enhancement of this activity thus leads to a reduction in the concentration of polyamino acids in the culture medium and has a positive effect according to the invention on the industrial fermentation of the relevant microorganisms. This enhancement of activity advantageously takes place at the genetic level. Methods for this are known per se. For example, mention may be made of the transfer of this gene to an expression vector: Such a vector can be introduced by transformation into the cells used for the fermentation and where appropriate be activated under certain conditions, so that the derived protein then acts in addition to the endogenously formed YwtD.

In preferred embodiments, both uses are those where the functional inactivation or increase in activity takes place during the fermentation of the microorganism, preferably with a reduction of the slime attributable to polyamino acids to 50%, particularly preferably to less than 20%, very particularly preferably to less than 5%, once again all intermediate integral or fractional percentages being understood in appropriately preferred gradation.

To determine these values, cells of an untreated strain and of a treated strain are fermented under conditions which are otherwise identical and suitably the viscosity of the respective medium is determined during the fermentation. Since the strains are otherwise identical, the differences in viscosity are attributable to the different contents of polyamino acids. Every reduction in viscosity is desired according to the invention. Comparable values as percentages are obtained by taking samples from both fermentations and determining the content of polyamino acid-containing slime by methods known per se. It is increasingly preferred for the value which can be determined in the sample of the invention to be at the transition into the stationary growth phase less than 50%, 40%, 30%, 20%, 10%, 5% and very especially less than 1% of the corresponding value for the comparative fermentation.

This is because the intention according to the problem was to improve the fermentation of the microorganisms employed for biotechnological production. Thus, it is worthwhile or, especially when a plurality of genes is affected, usually necessary to carry out the relevant molecular biological constructs on the laboratory scale and, where appropriate, on host cells which merely represent intermediate stages, for example construction of a deletion vector in E. coli. However, it is desired according to the invention for the inactivation of the genes ywsC, ywsC', ywtA or ywtB to show the hoped-for effects especially during the fermentation. The increase in the activity of the ywtD gene can be controlled for example via inducible promoters which are for example of the relevant transgene. The activity of this gene can thus be switched on deliberately by adding an inducer at a time which appears suitable during the fermentation. As an alternative thereto, this gene can also be coupled to a promoter which responds to stress signals, for instance to an oxygen content which is too low, as also occurs when mixing is inadequate in a fermenter which is blocked by slime.

In further preferred embodiments, these uses of the invention are such that, with increasing preference, 2, 3 or 4 of the genes ywsC, ywsC', ywtA and ywtB are inactivated, preferably in combination with an enhancement of the activity mediated by the ywtD gene.

It may be recalled at this point that in vivo in the relevant organisms it is probable that both the genes ywsC and ywsC' may not be present simultaneously, but in each case only one thereof. In these cases it is possible for a maximum of 3 of said genes to be inactivated, so that this then represents the most preferred embodiment in this respect.

This embodiment serves as safeguard in the event that the molecular biological form of the inactivation chosen for inactivation of one of these genes is incomplete and the cell still has corresponding residual activities. This applies in particular to host cells other than *B. subtilis* for which, according to Ashiuchi et al. (see above), it has been demonstrated that these genes are present in only one copy in each case. It appears to be particularly worthwhile to combine the deletion approach with that of enhancement of the activity mediated by the ywtD, because two systems which act differently in principle are thereby combined together.

In one embodiment of the use for functional inactivation of one or more of the genes ywsC, ywsC', ywtA and ywtB, a nucleic acid coding for an inactive protein and having a point mutation is employed.

Nucleic acids of this type can be generated by methods of point mutagenesis known per se. Such methods are described for example in relevant handbooks such as that of Fritsch, Sambrook and Maniatis "Molecular cloning: a laboratory manual", Cold Spring Harbor Laboratory Press, New York, 1989. In addition, numerous commercial construction kits are now available therefor, for instance the QuickChange® kit from Stratagene, La Jolla, USA. The principle thereof is for oligonucleotides having single exchanges (mismatch primers) to be synthesized and hybridized with the gene in single-stranded form; subsequent DNA polymerization then affords corresponding point mutants. It is possible to use for this purpose the respective species-specific sequences of these genes. Owing to the high homologies, it is possible and particularly advantageous according to the invention to carry out this reaction on the basis of the sequences provided by SEQ ID NO. 1, 3, 5 and 7. These sequences can also serve to design appropriate mismatch primers for related species, especially on the basis of the conserved regions identifiable in the alignments of FIGS. 6 to 10 and 1 to 5.

In one embodiment of this use, in each case a nucleic acid with a deletion mutation or insertion mutation is employed for the functional inactivation, preferably including the border sequences, in each case comprising at least 70 to 150 nucleic acid positions, of the region coding for the protein.

These methods are also familiar per se to the skilled worker. It is thus possible to prevent the formation of one or more of the factors YwsC, YwsC', YwtA and YwtB by the host cell by cutting out part of the relevant gene on an appropriate transformation vector via restriction endonucleases, and subsequently transforming the vector into the host of interest, where the active gene is replaced by the inactive copy via the homologous recombination which is still possible until then. In the embodiment of insertion mutation it is possible merely to introduce the intact gene interruptingly or, instead of a gene portion, another gene, for example a selection marker. Phenotypical checking of the mutation event is possible thereby in a manner known per se.

In order to enable these recombination events which are necessary in each case between the defective gene introduced into the cell and the intact gene copy which is endogenously present for example on the chromosome, it is necessary according to the current state of knowledge that in each case there is agreement in at least 70 to 150 connected nucleic acid positions, in each case in the two border sequences to the non-agreeing part, with the part lying between being immaterial. Accordingly, preferred embodiments are those including only two flanking regions with at least one of these sizes.

In an alternative embodiment of this use, nucleic acids having a total of two nucleic acid segments which in each case comprise at least 70 to 150 nucleic acid positions, and thus flank at least partly, preferably completely, the region coding for the protein, are employed. The flanking regions can in this connection be ascertained starting from the known sequences by methods known per se, for example with the aid of outwardly directed PCR primers and a preparation of genomic DNA as template (anchored PCR). This is because it is not obligatory for the segments to be protein-encoding in order to make it possible to exchange the two gene copies by homologous recombination. According to the present invention it is possible to design the primers required for this on the basis of SEQ ID NO. 1, 3, 5 and 7 also for other species of Gram-positive bacteria and, among these, in particular for those of the genus *Bacillus*. As an alternative to this experimental approach it is possible to take such regions which are at least in part non-coding for many of these genes from related species, for example from *B. subtilis* database entries, for example the SubtiList database of the Institute Pasteur, Paris, France.

A further preferred embodiment involves one of the described uses according to the invention in which an expression vector is employed for said enhancement of the activity mediated by the ywtD gene, preferably a vector which comprises this gene together with nucleic acid segments for regulating this gene.

As already stated above, the increased activity of this gene and thus of the derived protein can be deliberately regulated from outside thereby, or adapts automatically via the conditions prevailing in the fermentation medium to the need for a reduction in the polyamino acid concentration. It is particularly advantageous to use here for the nucleic acids of the invention described which code for ywtD, and very especially that according to SEQ ID NO. 9.

The present invention is also implemented in the form of genetically modified microorganisms, to which that stated above applies correspondingly.

These are very generally microorganisms in which at least one of the genes ywsC, ywsC', ywtA or ywtB is functionally inactivated or ywtD has enhanced activity.

These are preferably microorganisms in which, with increasing preference, 2, 3 or 4 of the genes ywsC, ywsC', ywtA or ywtB are inactivated, preferably in combination with an enhancement of the activity mediated by the ywtD gene.

These are preferably microorganisms in the form of bacteria.

The microorganisms among these which are preferred according to the statements hitherto are Gram-negative bacteria, especially those of the genera *Escherichia coli, Klebsiella, Pseudomonas* or *Xanthomonas*, especially strains of *E. coli* K12, *E. coli* B or *Klebsiella planticola*, and very especially derivatives of the strains *Escherichia coli* BL21 (DE3), *E. coli* RV308, *E. coli* DH5α, *E. coli* JM109, *E. coli* XL-1 or *Klebsiella planticola* (Rf).

Microorganisms which are not less preferred according to statements hitherto are Gram-positive bacteria, especially those of the genus *Bacillus, Staphylococcus* or *Corynebacterium*, very particularly of the species *Bacillus lentus, B. licheniformis, B. amyloliquefaciens, B. subtilis, B. globigii* or

*B. alcalophilus, Staphylococcus carnosus* or *Corynebacterium glutamicum* and, among these, very especially *B. licheniformis* DSM 13.

According to the problem on which the present application is based, the intention was primarily to improve industrial fermentation methods. Accordingly, the invention is implemented especially in corresponding fermentation methods of the invention.

These are very generally methods for the fermentation of a microorganism of the invention described above.

According to statements hitherto, the methods characterized thereby are correspondingly preferred. These include in particular the embodiment of one or more of the genes ywsC, ywsC', ywtA or ywtB being functionally inactivated or the activity of ywtD being enhanced, in particular combinations of the two approaches. For this purpose, recourse is particularly preferably had to the nucleic acids of the invention described above, especially those indicated under SEQ ID NO. 1, 3, 5, 7, or 9. This applies correspondingly also to the species selected as suitable for the respective fermentation. According to the statements above, those among these which are increasingly preferred have an increasing extent of relationship to *B. licheniformis* DSM13, because the prospects of success on use of the stated nucleic acids increase thereby.

Among the fermentation methods of the invention, those for preparing a valuable product are preferred, especially for preparing a low molecular weight compound or a protein.

This is because this is the most important area of application of industrial fermentations.

These are preferably methods where the low molecular weight compound is a natural product, a dietary supplement or a pharmaceutically relevant compound.

In this way for example amino acids or vitamins which are used in particular as dietary supplements are produced. Pharmaceutically relevant compounds may be precursors or intermediates for medicaments or even the latter themselves. In all these cases, the term biotransformation is also used, according to which the metabolic properties of the microorganisms are utilized to replace, entirely or at least in individual steps, the otherwise elaborate chemical synthesis.

No less preferred are corresponding methods in which the protein produced in this way is an enzyme, in particular one from the group of α-amylases, proteases, cellulases, lipases, oxidoreductases, peroxidases, laccases, oxidases and hemicellulases.

Industrial enzymes prepared by such methods are used for example in the food industry. Thus, α-amylases are used for example to prevent bread becoming stale or to clarify fruit juices. Proteases are used for the lysis of proteins. All these enzymes have been described for use in detergent and cleaner compositions, a prominent place being occupied in particular by the *Subtilisin* proteases prepared naturally by Gram-positive bacteria. They are used in particular in the textile and leather industries for processing the natural raw materials. A further possibility is for all these enzymes in turn to be employed in the context of biotransformation as catalysts for chemical reactions.

Many of these enzymes are originally derived from *Bacillus* species and are therefore produced particularly successfully in Gram-positive organisms, especially those of the genus *Bacillus*, including in many cases also derivatives of *B. licheniformis* DSM13. Production methods based on these microbial systems in particular can be improved with the aid of the present invention, because the sequences indicated in particular in SEQ ID NO. 1, 3, 5, 7 and 9 are derived from precisely this organism.

Finally, the factors made available with the present application can also be employed positively, meaning in the sense of their natural function, meaning in connection with a targeted preparation, modification or degradation of poly-gamma-glutamate.

One embodiment is thus formed by microbial methods for the preparation, modification or degradation of poly-gamma-glutamate in which one of the nucleic acids ywsC, ywsC', ywtA, ywtB and/or ywtD of the invention described above or a corresponding nucleic acid which codes a protein of the invention described above is employed transgenically, preferably to form the corresponding protein of the invention described above.

Preferred methods among these are those in which a microorganism from the genus *Bacillus*, in particular *B. subtilis* or *B. licheniformis*, is employed.

It is thus possible, as described for example in the applications JP 08308590 A or WO 02/055671 A1, to produce GLA microbially, specifically in *B. subtilis* and *B. licheniformis*. The DNA sequences made available with the present application can be utilized for example to increase the respective gene activities in appropriate cells, and thus to increase the yield.

As alternative thereto, cell-free methods for the preparation, modification or degradation of poly-gamma-glutamate are now also possible, involving a gene product YwsC, YwsC', YwtA, YwtB and/or YwtD of the invention described above, which is involved in the formation of polyamino acids, preferably with use of a corresponding nucleic acid of the invention described above.

Thus, these factors can be reacted for example in a bioreactor. The design of such enzyme bioreactors is known from the prior art.

Corresponding methods of this type which are particularly preferred among these are those where 2, preferably 3, particularly preferably 4, different ones of said gene products or nucleic acids are employed.

This is because the factors YwsC, YwtA and YwtB in particular usually form, as described in the introduction, a coherent complex, so that it is necessary to speak of a joint activity. Simultaneous or subsequent activity of YwtD might serve for example to influence the biophysical properties of the formed polyamino acid and, for example, for adaptation for use in cosmetic preparations.

The following examples illustrate the present invention further.

EXAMPLES

All molecular biological working steps follow standard methods as indicated for example in the handbook by Fritsch, Sambrook and Maniatis "Molecular cloning: a laboratory manual", Cold Spring Harbour Laboratory Press, New York, 1989, or comparable relevant works. Enzymes, construction kits and apparatuses were employed in accordance with the respective manufacturer's instructions.

Example 1

Identification of the Genes ywsC, ywsC', ywtA, ywtB and ywtD from *B. licheniformis* DSM 13

The genomic DNA was prepared by standard methods from the strain *B. licheniformis* DSM 13, which is available to anyone from the Deutsche Sammlung von Mikroorganismen and Zellkulturen GmbH, Mascheroder Weg 1b, 38124 Braunschweig, mechanically fractionated and fractionated by electrophoresis in a 0.8% agarose gel. For a shotgun cloning of the smaller fragments, the fragments 2 to 2.5 kb in size were eluted from the agarose gel, dephosphorylated and ligated as blunt-ended fragments into the SmaI restriction cleavage site of the vector pTZ19R-Cm. This is a derivative which confers chloramphenicol resistance of the plasmid pTZ19R which is obtainable from Fermentas (St. Leon-Rot). A gene library of the smaller fragments was obtained thereby. As second shotgun cloning, the genomic fragments obtained by a partial restriction with the enzyme SauIIIaI were ligated into the SuperCos 1 vector system ("Cosmid Vector Kit") from Stratagene, La Jolla, USA, resulting in a gene library over the predominantly larger fragments.

The relevant recombinant plasmids were isolated and sequenced from the bacteria E. coli DH5α (D. Hannahan (1983): "Studies on transformation on Escherichia coli"; J Mol. Microbiol., volume 166, pages 557-580) obtainable by transformation with the relevant gene libraries. The dye termination method (dye terminator chemistry) was employed in this case, carried out by the automatic sequencers MegaBACE 1000/4000 (Amersham Bioscience, Piscataway, USA) and ABI Prism 377 (Applied Biosystems, Foster City, USA).

In this way, inter alia the sequences SEQ ID NO. 1, 3, 5, 7 and 9 which are indicated in the sequence listing of the present application were obtained and stand in this sequence for the genes ywsC, ywsC' (as truncated variant of ywsC), ywtA, ywtB and ywtD. The amino acid sequences derived therefrom are indicated in the corresponding sequence in SEQ ID NO. 2, 4, 6, 8 and 10, respectively. A truncated variant ywsC' (or YwsC') is indicated for the gene or protein ywsC (or YwsC) because the comparison, shown in FIG. 6, of the amino acid sequences for the homologous protein in B. subtilis shows a polypeptide which is N-terminally shorter by 16 amino acids with otherwise quite high homology and therefore comparable activity.

Reproducibility

These genes and gene products can now be artificially synthesized by methods known per se, and without the need to reproduce the described sequencing, in a targeted manner on the basis of these sequences. It is possible, as further alternative thereto, to isolate the relevant genes from a Bacillus strain, in particular the strain B. licheniformis DSM 13 which is obtainable from the DSMZ, via PCR, it being possible to use the respective border sequences indicated in the sequence listing for synthesizing primers. If further strains are used, the genes homologous thereto in each case are obtained, and the success of the PCR should increase with the closeness of the relationship of the selected strains to B. licheniformis DSM 13, because this is likely to be associated with an increasing agreement of sequences also within the primer binding regions.

Example 2

Sequence Homologies

After ascertaining the DNA and amino acid sequences as in Example 1, in each case the most similar homologs disclosed to date were ascertained by a search in the databases GenBank (National Center for Biotechnology Information NCBI, National Institutes of Health, Bethesda, Md., USA) and Subtilist of the Institute Pasteur, Paris, France.

The ascertained DNA and amino acid sequences were compared with one another via the alignments depicted in FIGS. 1 to 10; the computer program used for this was Vector NTI® Suite Version 7 which is obtainable from Informax Inc., Bethesda, USA. In this case, the standard parameters of this program were used, meaning for comparison of the DNA sequences: K-tuple size: 2; Number of best Diagonals: 4; Window size: 4; Gap penalty: 5; Gap opening penalty: 15 and Gap extension penalty: 6.66. The following standard parameters applied to the comparison of the amino acid sequences: K-tuple size: 1; Number of best Diagonals: 5; Window size: 5; Gap penalty: 3; Gap opening penalty: 10 and Gap extension penalty: 0.1. The results of these sequence comparisons are compiled in Table 1 below, the accession numbers indicated being those from the NCBI database.

TABLE 1

Genes and proteins of greatest similarity to the genes and proteins found in Example 1.

| Gene or protein found in B. licheniformis/ SEQ ID NO. | Most closely related gene or protein | Database entry of the most closely related gene or protein | Homology in % identity |
| --- | --- | --- | --- |
| ywsC/1 | ywsC from B. subtilis | AB046355.1 | 75.4 |
| ywsC'/3 | ywsC from B. subtilis | AB046355.1 | 78.5 |
| ywtA/5 | ywsA from B. subtilis | AB046355.1 | 77.8 |
| ywtB/7 | ywsB from B. subtilis | AB046355.1 | 67.1 |
| ywtD/9 | ywtD from B. subtilis | AB080748 | 62.3 |
| YwsC/2 | YwsC from B. subtilis | AB046355.1 | 86.1 |
| YwsC'/4 | YwsC from B. subtilis | AB046355.1 | 89.6 |
| YwtA/6 | YwsA from B. subtilis | AB046355.1 | 89.9 |
| YwtB/8 | YwsB from B. subtilis | AB046355.1 | 65.8 |
| YwtD/10 | YwsD from B. subtilis | AB046355.1 | 57.3 |

It is evident that the found genes and the gene products derived therefrom are novel genes and proteins with a distinct difference from the prior art disclosed hitherto.

Example 3

Functional Inactivation of One or More of the Genes ywsC, ywsC', ywtA and ywtB in B. Licheniformis Principle of the Preparation of a Deletion Vector Each of these genes can be functionally inactivated, for example, by means of a so-called deletion vector. This procedure is described per se for example by J. Vehmaanperä et al. (1991) in the publication "Genetic manipulation of Bacillus amyloliquefaciens"; J. Biotechnol., volume 19, pages 221-240.

A suitable vector for this is pE194 which is characterized in the publication "Replication and incompatibility properties of plasmid pE194 in Bacillus subtilis" by T. J. Gryczan et al. (1982), J. Bacteriol., volume 152, pages 722-735. The advantage of this deletion vector is that it possesses a temperature-dependent origin of replication. pE194 is able to replicate in the transformed cell at 33° C., so that initial selection for successful transformation takes place at this temperature. Subsequently, the cells comprising the vector are incubated at 42° C. The deletion vector no longer replicates at this temperature, and a selection pressure is exerted on the integration of the plasmid via a previously selected homologous region into the chromosome. A second homologous recombination via a second homologous region then leads to excision of the vector together with the intact gene copy from the chromosome and thus to deletion of the gene which is located in the chromosome in vivo. Another possibility as second recombination would be the reverse reaction to integration, meaning recombination of the vector out of the chromosome, so that the chromosomal gene would remain intact. The gene deletion must therefore be detected by methods known per se, for instance in a Southern blot after restriction of the chromosomal DNA with suitable enzymes or with the aid of the PCR technique on the basis of the size of the amplified region.

It is thus necessary to select two homologous regions of the gene to be deleted, each of which should include 70 base pairs in each case, for example the 5' region and the 3' region of the selected gene. These are cloned into the vector in such a way that they flank a part coding for an inactive protein, or are in direct succession, omitting the region in between. The deletion vector is obtained thereby.

Deletion of the Genes ywsC, ywsC', ywtA and ywtB Considered Here

A deletion vector of the invention is constructed by PCR amplification of the 5' and 3' regions of one of these four or three genes. The sequences SEQ ID NO. 1, 3, 5 and 7 indicated in the sequence listing are available for designing suitable primers and originate from *B. licheniformis*, but ought also to be suitable, because of the homologies to be expected, for other species, especially of the genus *Bacillus*.

The two amplified regions suitably undergo intermediate cloning in direct succession on a vector useful for these operations, for example on the vector pUC18 which is suitable for cloning steps in *E. coli*.

The next step is a subcloning into the vector pE194 selected for deletion, and transformation thereof into *B. subtilis* DB104, for instance by the method of protoplast transformation according to Chang & Cohen (1979; "High Frequency Transformation of *Bacillus subtilis* Protoplasts by Plasmid DNA"; *Molec. Gen. Genet.* (1979), volume 168, pages 111-115). All working steps must be carried out at 33° C. in order to ensure replication of the vector.

In a next step, the vector which has undergone intermediate cloning is likewise transformed by the method of protoplast transformation into the desired host strain, in this case *B. licheniformis*. The transformants obtained in this way and identified as positive by conventional methods (selection via the resistance marker of the plasmid; check by plasmid preparation and PCR for the insert) are subsequently cultured at 42° C. under selection pressure for presence of the plasmid through addition of erythromycin. The deletion vector is unable to replicate at this temperature, and the only cells to survive are those in which the vector is integrated into the chromosome, and this integration most probably takes place in homologous or identical regions. Excision of the deletion vector can then be induced subsequently by culturing at 33° C. without erythromycin selection pressure, the chromosomally encoded gene being completely deleted from the chromosome. The success of the deletion is subsequently checked by Southern blotting after restriction of the chromosomal DNA with suitable enzymes or with the aid of the PCR technique.

Such transformants in which the relevant gene is deleted are additionally distinguished by a limitation or even complete inability to form GLA.

The invention claimed is:

1. An isolated microorganism of the genus *Bacillus* having at least one gene selected from the group consisting of:
    (a) functionally inactivated ywsC genes coding for a gene product involved in the formation of polyamino acids and having a nucleotide sequence which is at least 90% identical to the nucleotide sequence of SEQ ID NO. 1, (b) functionally inactivated ywsC' genes coding for a gene product involved in the formation of polyamino acids and having a nucleotide sequence which is at least 90% identical to the nucleotide sequence of SEQ ID NO. 3, (c) functionally inactivated ywtA genes coding for a gene product involved in the formation of polyamino acids and having a nucleotide sequence which is at least 90% identical to the nucleotide sequence of SEQ ID NO. 5, (d) functionally inactivated ywtB genes coding for a gene product involved in the formation of polyamino acids and having a nucleotide sequence which is at least 90% identical to the nucleotide sequence of SEQ ID NO. 7, and (e) functionally enhanced *Bacillus* ywtD genes coding for a gene product involved in the degradation of polyamino acids and having a nucleotide sequence which is at least 90% identical to the nucleotide sequence of SEQ ID NO. 9, wherein the ywsC, ywsC', ywtA and ywtB genes are functionally inactivated by introducing an insertion, deletion or point mutation in said gene, and the ywtD gene is functionally enhanced by placing the ywtD gene under control of a heterologous promoter or by increasing its copy number, and wherein the isolated microorganism is able to form polyamino acids prior to functional inactivation of the ywsC, ywsC', ywtA and ywtB genes and/or functional enhancement of the ywtD gene.

2. The microorganism according to claim 1, wherein said microorganism has a functionally enhanced *Bacillus* ywtD gene coding for a gene product involved in the degradation of polyamino acids and having a nucleotide sequence which is at least 90% identical to the nucleotide sequence of SEQ ID NO. 9, and wherein said microorganism further comprises at least one gene selected from the group consisting of:
  (a) functionally inactivated ywsC genes coding for a gene product involved in the formation of polyamino acids and having a nucleotide sequence which is at least 90% identical to the nucleotide sequence of SEQ ID NO. 1,
  (b) functionally inactivated ywsC' genes coding for a gene product involved in the formation of polyamino acids and having a nucleotide sequence which is at least 90% identical to the nucleotide sequence of SEQ ID NO. 3,
  (c) functionally inactivated ywtA genes coding for a gene product involved in the formation of polyamino acids and having a nucleotide sequence which is at least 90% identical to the nucleotide sequence of SEQ ID NO. 5, and
  (d) functionally inactivated ywtB genes coding for a gene product involved in the formation of polyamino acids and having a nucleotide sequence which is at least 90% identical to the nucleotide sequence of SEQ ID NO. 7,
  wherein the ywsC, ywsC', ywtA and ywtB genes are functionally inactivated by introducing an insertion, deletion or point mutation in said gene, and the ywtD gene is functionally enhanced by placing the ywtD gene under control of a heterologous promoter or by increasing its copy number,
  wherein the ywsC, ywsC', ywtA and ywtB genes, prior to functional inactivation, encode a protein involved in the formation of polyamino acids.

3. The microorganism according to claim 1, wherein said microorganism is a Gram-positive bacterium selected from the group consisting of the species *B. lentus, B. licheniformis, B. amyloliquefaciens, B. globigii*, and *B. alcalophilus*.

4. The microorganism according to claim 1, wherein said microorganism is a Gram-positive bacterium which is a derivative of *B. licheniformis* DSM 13.

5. An isolated *B. licheniformis* DSM13 microorganism having at least one gene selected from the group consisting of:
  (a) functionally inactivated ywsC genes coding for a gene product involved in the formation of polyamino acids and having a nucleotide sequence which is at least 90% identical to the nucleotide sequence of SEQ ID NO. 1,
  (b) functionally inactivated ywsC' genes coding for a gene product involved in the formation of polyamino acids and having a nucleotide sequence which is at least 90% identical to the nucleotide sequence of SEQ ID NO. 3,
  (c) functionally inactivated ywtA genes coding for a gene product involved in the formation of polyamino acids and having a nucleotide sequence which is at least 90% identical to the nucleotide sequence of SEQ ID NO. 5,
  (d) functionally inactivated ywtB genes coding for a gene product involved in the formation of polyamino acids and having a nucleotide sequence which is at least 90% identical to the nucleotide sequence of SEQ ID NO. 7, and
  (e) functionally enhanced *Bacillus* ywtD genes coding for a gene product involved in the degradation of polyamino acids and having a nucleotide sequence which is at least 90% identical to the nucleic acid sequence of SEQ ID NO. 9,
  wherein the ywsC, ywsC', ywtA and ywtB genes are functionally inactivated by introducing an insertion, deletion or point mutation in said gene, and the ywtD gene is functionally enhanced by placing the ywtD gene under control of a heterologous promoter or by increasing its copy number.

6. The isolated microorganism according to claim 5, wherein said microorganism has a functionally enhanced *Bacillus* ywtD gene coding for a gene product involved in the degradation of polyamino acids and having a nucleotide sequence which is at least 90% identical to the nucleic acid sequence of SEQ ID NO. 9, and wherein said microorganism further comprises at least one functionally inactivated gene selected from the group consisting of:
  (a) functionally inactivated ywsC genes coding for a gene product involved in the formation of polyamino acids and having a nucleotide sequence which is at least 90% identical to the nucleotide sequence of SEQ ID NO. 1,
  (b) functionally inactivated ywsC' genes coding for a gene product involved in the formation of polyamino acids and having a nucleotide sequence which is at least 90% identical to the nucleotide sequence of SEQ ID NO. 3,
  (c) functionally inactivated ywtA genes coding for a gene product involved in the formation of polyamino acids and having a nucleotide sequence which is at least 90% identical to the nucleotide sequence of SEQ ID NO. 5, and
  (d) functionally inactivated ywtB genes coding for a gene product involved in the formation of polyamino acids and having a nucleotide sequence which is at least 90% identical to the nucleotide sequence of SEQ ID NO. 6,
  wherein the ywsC, ywsC', ywtA and ywtB genes are functionally inactivated by introducing an insertion, deletion or point mutation in said gene, and the ywtD gene is functionally enhanced by placing the ywtD gene under control of a heterologous promoter or by increasing its copy number,
  wherein the ywsC, ywsC', ywtA and ywtB genes, prior to functional inactivation, encode a protein involved in the formation of polyamino acids.

7. The isolated microorganism according to claim 1 wherein the at least one gene is selected from the group consisting of:
  (a) functionally inactivated ywsC genes coding for a gene product involved in the formation of polyamino acids and having a nucleotide sequence which is at least 96% identical to the nucleotide sequence of SEQ ID NO. 1,
  (b) functionally inactivated ywsC' genes coding for a gene product involved in the formation of polyamino acids and having a nucleotide sequence which is at least 96% identical to the nucleotide sequence of SEQ ID NO. 3,
  (c) functionally inactivated ywtA genes coding for a gene product involved in the formation of polyamino acids and having a nucleotide sequence which is at least 96% identical to the nucleotide sequence of SEQ ID NO. 5,
  (d) functionally inactivated ywtB genes coding for a gene product involved in the formation of polyamino acids and having a nucleotide sequence which is at least 96% identical to the nucleotide sequence of SEQ ID NO. 7, and
  (e) functionally enhanced *Bacillus* ywtD genes coding for a gene product involved in the degradation of polyamino acids and having a nucleotide sequence which is at least 96% identical to the nucleotide sequence of SEQ ID NO. 9.

8. The isolated microorganism according to claim 1 wherein the at least one gene is a functionally inactivated gene inactivated by at least one point mutation, and wherein the functionally inactivated gene is selected from the group consisting of functionally inactivated ywsC, ywsC', ywtA and ywtB genes.

9. The isolated microorganism according to claim 8 wherein the at least one gene is a functionally inactivated gene inactivated by a single point mutation, and wherein the functionally inactivated gene is selected from the group consisting of functionally inactivated ywsC, ywsC', ywtA and ywtB genes.

10. The isolated microorganism according to claim 1 wherein the at least one gene is a functionally inactivated gene inactivated by at least one deletion mutation, and wherein the functionally inactivated gene is selected from the group consisting of functionally inactivated ywsC, ywsC', ywtA and ywtB genes.

11. The isolated microorganism according to claim 10 wherein the at least one gene is a functionally inactivated gene inactivated by a single deletion mutation, and wherein the functionally inactivated gene is selected from the group consisting of functionally inactivated ywsC, ywsC', ywtA and ywtB genes.

12. The isolated microorganism according to claim 1 wherein the at least one gene is a functionally inactivated gene inactivated by at least one insertion mutation, and wherein the functionally inactivated gene is selected from the group consisting of functionally inactivated ywsC, ywsC', ywtA and ywtB genes.

13. The isolated microorganism according to claim 12 wherein the at least one gene is a functionally inactivated gene inactivated by a single insertion mutation.

14. The isolated microorganism according to claim 1 wherein the at least one gene is the functionally enhanced *Bacillus* ywtD gene, and wherein the *Bacillus* ywtD gene is functionally enhanced by placing the ywtD gene under the control of an inducible promoter.

15. The isolated microorganism according to claim 1 wherein the at least one gene is the functionally enhanced *Bacillus* ywtD gene, and wherein the *Bacillus* ywtD gene is functionally enhanced by placing the ywtD gene under the control of a stress-signal responsive promoter.

16. The isolated microorganism according to claim 15 wherein the at least one gene is a functionally inactivated gene inactivated by at least one point mutation, and wherein the functionally inactivated gene is selected from the group consisting of functionally inactivated ywsC, ywsC', ywtA and ywtB genes.

17. The isolated microorganism according to claim 16 wherein the functionally inactivated gene is inactivated by a single point mutation.

18. The isolated microorganism according to claim 5 wherein the at least one gene is a functionally inactivated gene inactivated by at least one deletion mutation, and wherein the functionally inactivated gene is selected from the group consisting of functionally inactivated ywsC, ywsC', ywtA and ywtB genes.

19. The isolated microorganism according to claim 18 wherein the functionally inactivated gene is inactivated by a single deletion mutation.

20. The isolated microorganism according to claim 5 wherein the at least one gene is a functionally inactivated gene inactivated by at least one insertion mutation, and wherein the functionally inactivated gene is selected from the group consisting of functionally inactivated ywsC, ywsC', ywtA and ywtB genes.

21. The isolated microorganism according to claim 20 wherein the functionally inactivated gene is inactivated by a single insertion mutation.

22. The isolated microorganism according to claim 5 wherein the at least one gene is the functionally enhanced *Bacillus* ywtD gene, and wherein the *Bacillus* ywtD gene is functionally enhanced by placing the ywtD gene under the control of an inducible promoter.

23. The isolated microorganism according to claim 5 wherein the at least one gene is the functionally enhanced *Bacillus* ywtD gene and wherein the *Bacillus* ywtD gene is functionally enhanced by placing the ywtD gene under the control of a stress-signal responsive promoter.

* * * * *

SEQUENCE LISTING

```
<160> NUMBER OF SEQ ID NOS: 18

<210> SEQ ID NO 1
<211> LENGTH: 1230
<212> TYPE: DNA
<213> ORGANISM: Bacillus licheniformis DSM 13
<220> FEATURE:
<221> NAME/KEY: gene
<222> LOCATION: (1)..(1230)
<223> OTHER INFORMATION: ywsC
<220> FEATURE:
<221> NAME/KEY: CDS
<222> LOCATION: (1)..(1230)

<400> SEQUENCE: 1 atg aat gaa ttt aca tat cag att cca aga agg aga tgt aga caa aca     48
Met Asn Glu Phe Thr Tyr Gln Ile Pro Arg Arg Arg Cys Arg Gln Thr
1               5                   10                  15 atg tgg gta atg cta tta gcc tgt gtg atc gtt gtt ggg atc ggc att     96
Met Trp Val Met Leu Leu Ala Cys Val Ile Val Val Gly Ile Gly Ile
            20                  25                  30 tat gaa aaa agg cgc cac cag caa aat atc gat gcg ctg cct gtc cga    144
Tyr Glu Lys Arg Arg His Gln Gln Asn Ile Asp Ala Leu Pro Val Arg
        35                  40                  45 gtg aac atc aac ggt ata cgc gga aag tcc acg gtg aca aga tta aca    192
Val Asn Ile Asn Gly Ile Arg Gly Lys Ser Thr Val Thr Arg Leu Thr
    50                  55                  60 aca ggg ata tta atc gaa gca ggc tac aaa aca gta gga aaa aca acc    240
Thr Gly Ile Leu Ile Glu Ala Gly Tyr Lys Thr Val Gly Lys Thr Thr
65                  70                  75                  80 ggg aca gac gca agg atg att tat tgg gac aca ccg gaa gag aag ccg    288
Gly Thr Asp Ala Arg Met Ile Tyr Trp Asp Thr Pro Glu Glu Lys Pro
                85                  90                  95 atc aaa aga aag ccg caa ggg ccg aat atc gga gag cag aag gag gtt    336
```

```
Ile Lys Arg Lys Pro Gln Gly Pro Asn Ile Gly Glu Gln Lys Glu Val
            100                 105                 110 atg aaa gaa acg gtg gaa aga ggg gcc aat gcg att gtc agt gag tgc        384
Met Lys Glu Thr Val Glu Arg Gly Ala Asn Ala Ile Val Ser Glu Cys
        115                 120                 125 atg gcc gtt aat cct gat tac caa atc atc ttt cag gaa gaa ttg ctt        432
Met Ala Val Asn Pro Asp Tyr Gln Ile Ile Phe Gln Glu Glu Leu Leu
    130                 135                 140 cag gct aat atc ggc gtg atc gtg aac gtg ctg gag gat cac atg gat        480
Gln Ala Asn Ile Gly Val Ile Val Asn Val Leu Glu Asp His Met Asp
145                 150                 155                 160 gtg atg gga ccg act ttg gat gaa atc gca gaa gca ttc aca gca acc        528
Val Met Gly Pro Thr Leu Asp Glu Ile Ala Glu Ala Phe Thr Ala Thr
                165                 170                 175 att cct tat aat gga cat ttg gtt att act gat agt gag tat acc gat        576
Ile Pro Tyr Asn Gly His Leu Val Ile Thr Asp Ser Glu Tyr Thr Asp
            180                 185                 190 ttc ttt aag caa att gca aaa gaa agg aac aca aaa gtc atc gtc gca        624
Phe Phe Lys Gln Ile Ala Lys Glu Arg Asn Thr Lys Val Ile Val Ala
        195                 200                 205 gac aat tct aaa ata aca gat gaa tac ctc aga cag ttt gag tac atg        672
Asp Asn Ser Lys Ile Thr Asp Glu Tyr Leu Arg Gln Phe Glu Tyr Met
    210                 215                 220 gta ttc cct gat aat gcg tct ctt gcc ctc ggt gta gct caa gcg ttg        720
Val Phe Pro Asp Asn Ala Ser Leu Ala Leu Gly Val Ala Gln Ala Leu
225                 230                 235                 240 ggc att gac gaa gaa acc gcc ttt aaa ggc atg ctg aat gcg ccg cct        768
Gly Ile Asp Glu Glu Thr Ala Phe Lys Gly Met Leu Asn Ala Pro Pro
                245                 250                 255 gat ccg gga gcc atg aga att ctg ccg ctg atg aac gcc aag aat ccc        816
Asp Pro Gly Ala Met Arg Ile Leu Pro Leu Met Asn Ala Lys Asn Pro
            260                 265                 270 gga cat ttc gtc aac ggt ttt gcg gcc aat gac gca gct tcc act tta        864
Gly His Phe Val Asn Gly Phe Ala Ala Asn Asp Ala Ala Ser Thr Leu
        275                 280                 285 aac att tgg aag cgt gta aaa gaa ata ggc tat cct acg gat cag ccg        912
Asn Ile Trp Lys Arg Val Lys Glu Ile Gly Tyr Pro Thr Asp Gln Pro
    290                 295                 300 atc gtc att atg aac tgc cgc gcc gac agg gta gac aga aca cag cag        960
Ile Val Ile Met Asn Cys Arg Ala Asp Arg Val Asp Arg Thr Gln Gln
305                 310                 315                 320 ttt gcg gaa gat gtc ctt cct tat att gaa gca agt gaa ctt gtg ctg       1008
Phe Ala Glu Asp Val Leu Pro Tyr Ile Glu Ala Ser Glu Leu Val Leu
                325                 330                 335 att gga gaa aca aca gag ccg atc gtc aaa gca tat gaa gca ggc aaa       1056
Ile Gly Glu Thr Thr Glu Pro Ile Val Lys Ala Tyr Glu Ala Gly Lys
            340                 345                 350 att cct gcg gac aag ctg ttt gat ttt gag cac aaa tca acg gaa gaa       1104
Ile Pro Ala Asp Lys Leu Phe Asp Phe Glu His Lys Ser Thr Glu Glu
        355                 360                 365 atc atg ttc atg ctg aaa aac aag ctt gag ggc cgc gtt att tac gga       1152
Ile Met Phe Met Leu Lys Asn Lys Leu Glu Gly Arg Val Ile Tyr Gly
    370                 375                 380 gtc gga aat atc cac gga gca gcg gag cct ctc att gaa aaa ata caa       1200
Val Gly Asn Ile His Gly Ala Ala Glu Pro Leu Ile Glu Lys Ile Gln
385                 390                 395                 400 gat tac aag att aag cag ctc gtt agc tag                               1230
Asp Tyr Lys Ile Lys Gln Leu Val Ser
                405
```

```
<210> SEQ ID NO 2
<211> LENGTH: 409
<212> TYPE: PRT
<213> ORGANISM: Bacillus licheniformis DSM 13

<400> SEQUENCE: 2

Met Asn Glu Phe Thr Tyr Gln Ile Pro Arg Arg Cys Arg Gln Thr
 1               5                  10                  15

Met Trp Val Met Leu Leu Ala Cys Val Ile Val Gly Ile Gly Ile
             20                  25                  30

Tyr Glu Lys Arg Arg His Gln Gln Asn Ile Asp Ala Leu Pro Val Arg
             35                  40                  45

Val Asn Ile Asn Gly Ile Arg Gly Lys Ser Thr Val Thr Arg Leu Thr
 50                  55                  60

Thr Gly Ile Leu Ile Glu Ala Gly Tyr Lys Thr Val Gly Lys Thr Thr
 65                  70                  75                  80

Gly Thr Asp Ala Arg Met Ile Tyr Trp Asp Thr Pro Glu Glu Lys Pro
                 85                  90                  95

Ile Lys Arg Lys Pro Gln Gly Pro Asn Ile Gly Glu Gln Lys Glu Val
            100                 105                 110

Met Lys Glu Thr Val Glu Arg Gly Ala Asn Ala Ile Val Ser Glu Cys
            115                 120                 125

Met Ala Val Asn Pro Asp Tyr Gln Ile Ile Phe Gln Glu Glu Leu Leu
130                 135                 140

Gln Ala Asn Ile Gly Val Ile Val Asn Val Leu Glu Asp His Met Asp
145                 150                 155                 160

Val Met Gly Pro Thr Leu Asp Glu Ile Ala Glu Ala Phe Thr Ala Thr
                165                 170                 175

Ile Pro Tyr Asn Gly His Leu Val Ile Thr Asp Ser Glu Tyr Thr Asp
                180                 185                 190

Phe Phe Lys Gln Ile Ala Lys Glu Arg Asn Thr Lys Val Ile Val Ala
            195                 200                 205

Asp Asn Ser Lys Ile Thr Asp Glu Tyr Leu Arg Gln Phe Glu Tyr Met
210                 215                 220

Val Phe Pro Asp Asn Ala Ser Leu Ala Leu Gly Val Ala Gln Ala Leu
225                 230                 235                 240

Gly Ile Asp Glu Glu Thr Ala Phe Lys Gly Met Leu Asn Ala Pro Pro
                245                 250                 255

Asp Pro Gly Ala Met Arg Ile Leu Pro Leu Met Asn Ala Lys Asn Pro
            260                 265                 270

Gly His Phe Val Asn Gly Phe Ala Ala Asn Asp Ala Ala Ser Thr Leu
            275                 280                 285

Asn Ile Trp Lys Arg Val Lys Glu Ile Gly Tyr Pro Thr Asp Gln Pro
        290                 295                 300

Ile Val Ile Met Asn Cys Arg Ala Asp Arg Val Asp Arg Thr Gln Gln
305                 310                 315                 320

Phe Ala Glu Asp Val Leu Pro Tyr Ile Glu Ala Ser Glu Leu Val Leu
                325                 330                 335

Ile Gly Glu Thr Thr Glu Pro Ile Val Lys Ala Tyr Glu Ala Gly Lys
            340                 345                 350

Ile Pro Ala Asp Lys Leu Phe Asp Phe Glu His Lys Ser Thr Glu Glu
        355                 360                 365

Ile Met Phe Met Leu Lys Asn Lys Leu Glu Gly Arg Val Ile Tyr Gly
370                 375                 380
```

```
Val Gly Asn Ile His Gly Ala Ala Glu Pro Leu Ile Glu Lys Ile Gln
385                 390                 395                 400

Asp Tyr Lys Ile Lys Gln Leu Val Ser
                405

<210> SEQ ID NO 3
<211> LENGTH: 1182
<212> TYPE: DNA
<213> ORGANISM: Bacillus licheniformis DSM 13
<220> FEATURE:
<221> NAME/KEY: gene
<222> LOCATION: (1)..(1182)
<223> OTHER INFORMATION: ywsC'
<220> FEATURE:
<221> NAME/KEY: CDS
<222> LOCATION: (1)..(1182)

<400> SEQUENCE: 3 atg tgg gta atg cta tta gcc tgt gtg atc gtt gtt ggg atc ggc att     48
Met Trp Val Met Leu Leu Ala Cys Val Ile Val Val Gly Ile Gly Ile
1               5                   10                  15 tat gaa aaa agg cgc cac cag caa aat atc gat gcg ctg cct gtc cga     96
Tyr Glu Lys Arg Arg His Gln Gln Asn Ile Asp Ala Leu Pro Val Arg
            20                  25                  30 gtg aac atc aac ggt ata cgc gga aag tcc acg gtg aca aga tta aca    144
Val Asn Ile Asn Gly Ile Arg Gly Lys Ser Thr Val Thr Arg Leu Thr
        35                  40                  45 aca ggg ata tta atc gaa gca ggc tac aaa aca gta gga aaa aca acc    192
Thr Gly Ile Leu Ile Glu Ala Gly Tyr Lys Thr Val Gly Lys Thr Thr
    50                  55                  60 ggg aca gac gca agg atg att tat tgg gac aca ccg gaa gag aag ccg    240
Gly Thr Asp Ala Arg Met Ile Tyr Trp Asp Thr Pro Glu Glu Lys Pro
65                  70                  75                  80 atc aaa aga aag ccg caa ggg ccg aat atc gga gag cag aag gag gtt    288
Ile Lys Arg Lys Pro Gln Gly Pro Asn Ile Gly Glu Gln Lys Glu Val
                85                  90                  95 atg aaa gaa acg gtg gaa aga ggg gcc aat gcg att gtc agt gag tgc    336
Met Lys Glu Thr Val Glu Arg Gly Ala Asn Ala Ile Val Ser Glu Cys
            100                 105                 110 atg gcc gtt aat cct gat tac caa atc atc ttt cag gaa gaa ttg ctt    384
Met Ala Val Asn Pro Asp Tyr Gln Ile Ile Phe Gln Glu Glu Leu Leu
        115                 120                 125 cag gct aat atc ggc gtg atc gtg aac gtg ctg gag gat cac atg gat    432
Gln Ala Asn Ile Gly Val Ile Val Asn Val Leu Glu Asp His Met Asp
    130                 135                 140 gtg atg gga ccg act ttg gat gaa atc gca gaa gca ttc aca gca acc    480
Val Met Gly Pro Thr Leu Asp Glu Ile Ala Glu Ala Phe Thr Ala Thr
145                 150                 155                 160 att cct tat aat gga cat ttg gtt att act gat agt gag tat acc gat    528
Ile Pro Tyr Asn Gly His Leu Val Ile Thr Asp Ser Glu Tyr Thr Asp
                165                 170                 175 ttc ttt aag caa att gca aaa gaa agg aac aca aaa gtc atc gtc gca    576
Phe Phe Lys Gln Ile Ala Lys Glu Arg Asn Thr Lys Val Ile Val Ala
            180                 185                 190 gac aat tct aaa ata aca gat gaa tac ctc aga cag ttt gag tac atg    624
Asp Asn Ser Lys Ile Thr Asp Glu Tyr Leu Arg Gln Phe Glu Tyr Met
        195                 200                 205 gta ttc cct gat aat gcg tct ctt gcg ctc ggt gta gct caa gcg ttg    672
Val Phe Pro Asp Asn Ala Ser Leu Ala Leu Gly Val Ala Gln Ala Leu
    210                 215                 220 ggc att gac gaa gaa acc gcc ttt aaa ggc atg ctg aat gcg ccg cct    720
Gly Ile Asp Glu Glu Thr Ala Phe Lys Gly Met Leu Asn Ala Pro Pro
```

```
Gly Ile Asp Glu Glu Thr Ala Phe Lys Gly Met Leu Asn Ala Pro Pro
225                 230                 235                 240 gat ccg gga gcc atg aga att ctg ccg ctg atg aac gcc aag aat ccc       768
Asp Pro Gly Ala Met Arg Ile Leu Pro Leu Met Asn Ala Lys Asn Pro
                    245                 250                 255 gga cat ttc gtc aac ggt ttt gcg gcc aat gac gca gct tcc act tta       816
Gly His Phe Val Asn Gly Phe Ala Ala Asn Asp Ala Ala Ser Thr Leu
                260                 265                 270 aac att tgg aag cgt gta aaa gaa ata ggc tat cct acg gat cag ccg       864
Asn Ile Trp Lys Arg Val Lys Glu Ile Gly Tyr Pro Thr Asp Gln Pro
            275                 280                 285 atc gtc att atg aac tgc cgc gcc gac agg gta gac aga aca cag cag       912
Ile Val Ile Met Asn Cys Arg Ala Asp Arg Val Asp Arg Thr Gln Gln
        290                 295                 300 ttt gcg gaa gat gtc ctt cct tat att gaa gca agt gaa ctt gtg ctg       960
Phe Ala Glu Asp Val Leu Pro Tyr Ile Glu Ala Ser Glu Leu Val Leu
305                 310                 315                 320 att gga gaa aca aca gag ccg atc gtc aaa gca tat gaa gca ggc aaa      1008
Ile Gly Glu Thr Thr Glu Pro Ile Val Lys Ala Tyr Glu Ala Gly Lys
                    325                 330                 335 att cct gcg gac aag ctg ttt gat ttt gag cac aaa tca acg gaa gaa      1056
Ile Pro Ala Asp Lys Leu Phe Asp Phe Glu His Lys Ser Thr Glu Glu
                340                 345                 350 atc atg ttc atg ctg aaa aac aag ctt gag ggc cgc gtt att tac gga      1104
Ile Met Phe Met Leu Lys Asn Lys Leu Glu Gly Arg Val Ile Tyr Gly
            355                 360                 365 gtc gga aat atc cac gga gca gcg gag cct ctc att gaa aaa ata caa      1152
Val Gly Asn Ile His Gly Ala Ala Glu Pro Leu Ile Glu Lys Ile Gln
        370                 375                 380 gat tac aag att aag cag ctc gtt agc tag                              1182
Asp Tyr Lys Ile Lys Gln Leu Val Ser
385                 390

<210> SEQ ID NO 4
<211> LENGTH: 393
<212> TYPE: PRT
<213> ORGANISM: Bacillus licheniformis DSM 13

<400> SEQUENCE: 4

Met Trp Val Met Leu Leu Ala Cys Val Ile Val Gly Ile Gly Ile
1               5                   10                  15

Tyr Glu Lys Arg Arg His Gln Gln Asn Ile Asp Ala Leu Pro Val Arg
                20                  25                  30

Val Asn Ile Asn Gly Ile Arg Gly Lys Ser Thr Val Thr Arg Leu Thr
            35                  40                  45

Thr Gly Ile Leu Ile Glu Ala Gly Tyr Lys Thr Val Gly Lys Thr Thr
        50                  55                  60

Gly Thr Asp Ala Arg Met Ile Tyr Trp Asp Thr Pro Glu Glu Lys Pro
65                  70                  75                  80

Ile Lys Arg Lys Pro Gln Gly Pro Asn Ile Gly Glu Gln Lys Glu Val
                85                  90                  95

Met Lys Glu Thr Val Glu Arg Gly Ala Asn Ala Ile Val Ser Glu Cys
                100                 105                 110

Met Ala Val Asn Pro Asp Tyr Gln Ile Ile Phe Gln Glu Glu Leu Leu
            115                 120                 125

Gln Ala Asn Ile Gly Val Ile Val Asn Val Leu Glu Asp His Met Asp
        130                 135                 140

Val Met Gly Pro Thr Leu Asp Glu Ile Ala Glu Ala Phe Thr Ala Thr
```

```
                145                 150                 155                 160
Ile Pro Tyr Asn Gly His Leu Val Ile Thr Asp Ser Glu Tyr Thr Asp
                165                 170                 175

Phe Phe Lys Gln Ile Ala Lys Glu Arg Asn Thr Lys Val Ile Val Ala
            180                 185                 190

Asp Asn Ser Lys Ile Thr Asp Glu Tyr Leu Arg Gln Phe Glu Tyr Met
        195                 200                 205

Val Phe Pro Asp Asn Ala Ser Leu Ala Leu Gly Val Ala Gln Ala Leu
    210                 215                 220

Gly Ile Asp Glu Glu Thr Ala Phe Lys Gly Met Leu Asn Ala Pro Pro
225                 230                 235                 240

Asp Pro Gly Ala Met Arg Ile Leu Pro Leu Met Asn Ala Lys Asn Pro
                245                 250                 255

Gly His Phe Val Asn Gly Phe Ala Ala Asn Asp Ala Ala Ser Thr Leu
            260                 265                 270

Asn Ile Trp Lys Arg Val Lys Glu Ile Gly Tyr Pro Thr Asp Gln Pro
        275                 280                 285

Ile Val Ile Met Asn Cys Arg Ala Asp Arg Val Asp Arg Thr Gln Gln
    290                 295                 300

Phe Ala Glu Asp Val Leu Pro Tyr Ile Glu Ala Ser Glu Leu Val Leu
305                 310                 315                 320

Ile Gly Glu Thr Thr Glu Pro Ile Val Lys Ala Tyr Glu Ala Gly Lys
                325                 330                 335

Ile Pro Ala Asp Lys Leu Phe Asp Phe Glu His Lys Ser Thr Glu Glu
            340                 345                 350

Ile Met Phe Met Leu Lys Asn Lys Leu Glu Gly Arg Val Ile Tyr Gly
        355                 360                 365

Val Gly Asn Ile His Gly Ala Ala Glu Pro Leu Ile Glu Lys Ile Gln
    370                 375                 380

Asp Tyr Lys Ile Lys Gln Leu Val Ser
385                 390

<210> SEQ ID NO 5
<211> LENGTH: 450
<212> TYPE: DNA
<213> ORGANISM: Bacillus licheniformis DSM 13
<220> FEATURE:
<221> NAME/KEY: gene
<222> LOCATION: (1)..(450)
<223> OTHER INFORMATION: ywtA
<220> FEATURE:
<221> NAME/KEY: CDS
<222> LOCATION: (1)..(450)

<400> SEQUENCE: 5 atg ttt gga tca gat tta tat atc gcc ctc att tta gga gtc tta ctc     48
Met Phe Gly Ser Asp Leu Tyr Ile Ala Leu Ile Leu Gly Val Leu Leu
1               5                   10                  15 agt ttg att ttt gca gag aaa acg gga att gta cca gcc ggc ctc gtc     96
Ser Leu Ile Phe Ala Glu Lys Thr Gly Ile Val Pro Ala Gly Leu Val
            20                  25                  30 gta ccg ggt tat ttg gga ctt gtc ttc aat cag ccg att ttc atg ctg    144
Val Pro Gly Tyr Leu Gly Leu Val Phe Asn Gln Pro Ile Phe Met Leu
        35                  40                  45 ctc gtt ctt ttt gtc agt ttg ctg acg tat gtc atc gtg aaa ttc gga    192
Leu Val Leu Phe Val Ser Leu Leu Thr Tyr Val Ile Val Lys Phe Gly
    50                  55                  60 ctt tcc aaa att atg att cta tac gga cgc aga aaa ttc gca gca atg    240
```

```
Leu Ser Lys Ile Met Ile Leu Tyr Gly Arg Arg Lys Phe Ala Ala Met
 65                  70                  75                  80 ctg att acg gga att ctt ttg aaa atc ggt ttt gat ttt ata tat ccg    288
Leu Ile Thr Gly Ile Leu Leu Lys Ile Gly Phe Asp Phe Ile Tyr Pro
             85                  90                  95 gtg atg ccg ttt gag att gcc gaa ttc agg gga atc gga atc atc gtg    336
Val Met Pro Phe Glu Ile Ala Glu Phe Arg Gly Ile Gly Ile Ile Val
            100                 105                 110 ccg ggg ctg atc gcc aat acc att caa aga cag gga tta acg att acg    384
Pro Gly Leu Ile Ala Asn Thr Ile Gln Arg Gln Gly Leu Thr Ile Thr
        115                 120                 125 ctt gga agt acg ctt tta ttg agc gga gca aca ttc gtc att atg tat    432
Leu Gly Ser Thr Leu Leu Leu Ser Gly Ala Thr Phe Val Ile Met Tyr
    130                 135                 140 gct tac tat cta atc taa                                            450
Ala Tyr Tyr Leu Ile
145

<210> SEQ ID NO 6
<211> LENGTH: 149
<212> TYPE: PRT
<213> ORGANISM: Bacillus licheniformis DSM 13

<400> SEQUENCE: 6

Met Phe Gly Ser Asp Leu Tyr Ile Ala Leu Ile Leu Gly Val Leu Leu
  1               5                  10                  15

Ser Leu Ile Phe Ala Glu Lys Thr Gly Ile Val Pro Ala Gly Leu Val
             20                  25                  30

Val Pro Gly Tyr Leu Gly Leu Val Phe Asn Gln Pro Ile Phe Met Leu
         35                  40                  45

Leu Val Leu Phe Val Ser Leu Leu Thr Tyr Val Ile Val Lys Phe Gly
     50                  55                  60

Leu Ser Lys Ile Met Ile Leu Tyr Gly Arg Arg Lys Phe Ala Ala Met
 65                  70                  75                  80

Leu Ile Thr Gly Ile Leu Leu Lys Ile Gly Phe Asp Phe Ile Tyr Pro
             85                  90                  95

Val Met Pro Phe Glu Ile Ala Glu Phe Arg Gly Ile Gly Ile Ile Val
            100                 105                 110

Pro Gly Leu Ile Ala Asn Thr Ile Gln Arg Gln Gly Leu Thr Ile Thr
        115                 120                 125

Leu Gly Ser Thr Leu Leu Leu Ser Gly Ala Thr Phe Val Ile Met Tyr
    130                 135                 140

Ala Tyr Tyr Leu Ile
145

<210> SEQ ID NO 7
<211> LENGTH: 1170
<212> TYPE: DNA
<213> ORGANISM: Bacillus licheniformis DSM 13
<220> FEATURE:
<221> NAME/KEY: gene
<222> LOCATION: (1)..(1170)
<223> OTHER INFORMATION: ywtB
<220> FEATURE:
<221> NAME/KEY: CDS
<222> LOCATION: (1)..(1170)

<400> SEQUENCE: 7 atg aaa aaa caa ctg aac ttt cag gaa aaa ctg ctg aag ttg acg aag     48
Met Lys Lys Gln Leu Asn Phe Gln Glu Lys Leu Leu Lys Leu Thr Lys
  1               5                  10                  15
```

```
cag gag aaa aag aaa aca aac aag cac gtc ttt atc gta ttg ccc gtt      96
Gln Glu Lys Lys Lys Thr Asn Lys His Val Phe Ile Val Leu Pro Val
             20                  25                  30 att ttc tgt tta atg ttt gtc ttt act tgg gtc gga agc gcc aaa act     144
Ile Phe Cys Leu Met Phe Val Phe Thr Trp Val Gly Ser Ala Lys Thr
         35                  40                  45 cct tcg caa atg gac aaa aaa gaa gat gcc aag ctt aca gct act ttt     192
Pro Ser Gln Met Asp Lys Lys Glu Asp Ala Lys Leu Thr Ala Thr Phe
 50                  55                  60 gtt ggc gat atc atg atg gga aga aac gta gaa aaa gtg aca aac ttg     240
Val Gly Asp Ile Met Met Gly Arg Asn Val Glu Lys Val Thr Asn Leu
 65                  70                  75                  80 cac ggt tcg gaa agt gtc ttc aaa aat gtg aag ccg tac ttt aat gtg     288
His Gly Ser Glu Ser Val Phe Lys Asn Val Lys Pro Tyr Phe Asn Val
                 85                  90                  95 tca gat ttt atc aca gga aac ttt gaa aac cct gta acc aat gca aag     336
Ser Asp Phe Ile Thr Gly Asn Phe Glu Asn Pro Val Thr Asn Ala Lys
            100                 105                 110 gac tat caa gag gca gaa aag aac atc cat ctg caa acg aat caa gaa     384
Asp Tyr Gln Glu Ala Glu Lys Asn Ile His Leu Gln Thr Asn Gln Glu
        115                 120                 125 tca gtc gaa aca ttg aaa aag ctg aac ttc agc gta ctg aat ttt gcc     432
Ser Val Glu Thr Leu Lys Lys Leu Asn Phe Ser Val Leu Asn Phe Ala
130                 135                 140 aac aac cat gcg atg gac tac ggg gaa gac ggt ttg aag gat acg ctc     480
Asn Asn His Ala Met Asp Tyr Gly Glu Asp Gly Leu Lys Asp Thr Leu
145                 150                 155                 160 aat aaa ttt tca aat gag aat ctg gag ctt gtc gga gca gga aat aat     528
Asn Lys Phe Ser Asn Glu Asn Leu Glu Leu Val Gly Ala Gly Asn Asn
                165                 170                 175 ctt gaa gac gcg aaa cag cac gta tcc tat cag aat gtg aac ggc gta     576
Leu Glu Asp Ala Lys Gln His Val Ser Tyr Gln Asn Val Asn Gly Val
            180                 185                 190 aaa att gca acg ctc ggt ttt aca gac gtc tac aca aag aac ttt aca     624
Lys Ile Ala Thr Leu Gly Phe Thr Asp Val Tyr Thr Lys Asn Phe Thr
        195                 200                 205 gcc aaa aag aac aga ggc gga gtg ctg ccg ctc agt ccg aaa atc ttt     672
Ala Lys Lys Asn Arg Gly Gly Val Leu Pro Leu Ser Pro Lys Ile Phe
210                 215                 220 att cca atg att gcg gaa gca tcg aaa aaa gcg gat ctt gtc ctt gtc     720
Ile Pro Met Ile Ala Glu Ala Ser Lys Lys Ala Asp Leu Val Leu Val
225                 230                 235                 240 cat gtg cac tgg gga caa gaa tat gac aat gaa ccg aac gac aga cag     768
His Val His Trp Gly Gln Glu Tyr Asp Asn Glu Pro Asn Asp Arg Gln
                245                 250                 255 aag gat ctg gcc aag gcg att gca gat gcc gga gca gat gtc atc atc     816
Lys Asp Leu Ala Lys Ala Ile Ala Asp Ala Gly Ala Asp Val Ile Ile
            260                 265                 270 ggc gct cat ccc cat gtt ctc gaa ccg atc gaa gta tat aac ggt act     864
Gly Ala His Pro His Val Leu Glu Pro Ile Glu Val Tyr Asn Gly Thr
        275                 280                 285 gtg att ttc tac agc ctc ggc aac ttt gta ttt gat cag ggc tgg tca     912
Val Ile Phe Tyr Ser Leu Gly Asn Phe Val Phe Asp Gln Gly Trp Ser
290                 295                 300 aga aca cgg gac agc gcg ctt gta caa tac cat tta atg aat gac ggc     960
Arg Thr Arg Asp Ser Ala Leu Val Gln Tyr His Leu Met Asn Asp Gly
305                 310                 315                 320 aaa ggg cgc ttt gag gta acg cct ctc aac att cgc gaa gca acg ccg    1008
Lys Gly Arg Phe Glu Val Thr Pro Leu Asn Ile Arg Glu Ala Thr Pro
```

```
                   325                 330                 335
acg cct tta ggc aag agc gac ttc tta aaa cga aaa gcg atc ttc cgt    1056
Thr Pro Leu Gly Lys Ser Asp Phe Leu Lys Arg Lys Ala Ile Phe Arg
        340                 345                 350 caa ttg aca aaa gga aca aac ctc gac tgg aaa gaa gag aac gga aaa    1104
Gln Leu Thr Lys Gly Thr Asn Leu Asp Trp Lys Glu Glu Asn Gly Lys
            355                 360                 365 tta acg ttt gaa gtc gat cat gcg gac aag ctg aaa aat aat aaa aac    1152
Leu Thr Phe Glu Val Asp His Ala Asp Lys Leu Lys Asn Asn Lys Asn
370                 375                 380 gga gtg gtg aac aaa tga                                            1170
Gly Val Val Asn Lys
385

<210> SEQ ID NO 8
<211> LENGTH: 389
<212> TYPE: PRT
<213> ORGANISM: Bacillus licheniformis DSM 13

<400> SEQUENCE: 8

Met Lys Lys Gln Leu Asn Phe Gln Glu Lys Leu Leu Lys Leu Thr Lys
1               5                   10                  15

Gln Glu Lys Lys Lys Thr Asn Lys His Val Phe Ile Val Leu Pro Val
            20                  25                  30

Ile Phe Cys Leu Met Phe Val Phe Thr Trp Val Gly Ser Ala Lys Thr
        35                  40                  45

Pro Ser Gln Met Asp Lys Lys Glu Asp Ala Lys Leu Thr Ala Thr Phe
    50                  55                  60

Val Gly Asp Ile Met Met Gly Arg Asn Val Glu Lys Val Thr Asn Leu
65                  70                  75                  80

His Gly Ser Glu Ser Val Phe Lys Asn Val Lys Pro Tyr Phe Asn Val
                85                  90                  95

Ser Asp Phe Ile Thr Gly Asn Phe Glu Asn Pro Val Thr Asn Ala Lys
            100                 105                 110

Asp Tyr Gln Glu Ala Glu Lys Asn Ile His Leu Gln Thr Asn Gln Glu
        115                 120                 125

Ser Val Glu Thr Leu Lys Lys Leu Asn Phe Ser Val Leu Asn Phe Ala
    130                 135                 140

Asn Asn His Ala Met Asp Tyr Gly Glu Asp Gly Leu Lys Asp Thr Leu
145                 150                 155                 160

Asn Lys Phe Ser Asn Glu Asn Leu Glu Leu Val Gly Ala Gly Asn Asn
                165                 170                 175

Leu Glu Asp Ala Lys Gln His Val Ser Tyr Gln Asn Val Asn Gly Val
            180                 185                 190

Lys Ile Ala Thr Leu Gly Phe Thr Asp Val Tyr Thr Lys Asn Phe Thr
        195                 200                 205

Ala Lys Lys Asn Arg Gly Gly Val Leu Pro Leu Ser Pro Lys Ile Phe
    210                 215                 220

Ile Pro Met Ile Ala Glu Ala Ser Lys Lys Ala Asp Leu Val Leu Val
225                 230                 235                 240

His Val His Trp Gly Gln Glu Tyr Asp Asn Glu Pro Asn Asp Arg Gln
                245                 250                 255

Lys Asp Leu Ala Lys Ala Ile Ala Asp Ala Gly Ala Asp Val Ile Ile
            260                 265                 270

Gly Ala His Pro His Val Leu Glu Pro Ile Glu Val Tyr Asn Gly Thr
        275                 280                 285
```

-continued

```
Val Ile Phe Tyr Ser Leu Gly Asn Phe Val Phe Asp Gln Gly Trp Ser
    290                 295                 300
Arg Thr Arg Asp Ser Ala Leu Val Gln Tyr His Leu Met Asn Asp Gly
305                 310                 315                 320
Lys Gly Arg Phe Glu Val Thr Pro Leu Asn Ile Arg Glu Ala Thr Pro
                325                 330                 335
Thr Pro Leu Gly Lys Ser Asp Phe Leu Arg Lys Ala Ile Phe Arg
            340                 345                 350
Gln Leu Thr Lys Gly Thr Asn Leu Asp Trp Lys Glu Asn Gly Lys
        355                 360                 365
Leu Thr Phe Glu Val Asp His Ala Asp Lys Leu Lys Asn Asn Lys Asn
    370                 375                 380
Gly Val Val Asn Lys
385
```

<210> SEQ ID NO 9
<211> LENGTH: 1245
<212> TYPE: DNA
<213> ORGANISM: Bacillus licheniformis DSM 13
<220> FEATURE:
<221> NAME/KEY: gene
<222> LOCATION: (1)..(1245)
<223> OTHER INFORMATION: ywtD
<220> FEATURE:
<221> NAME/KEY: CDS
<222> LOCATION: (1)..(1245)
<220> FEATURE:
<221> NAME/KEY: misc_feature
<222> LOCATION: (1)..(3)
<223> OTHER INFORMATION: First codon translated as Met.

<400> SEQUENCE: 9

```
ttg ata aaa aaa gcg gca aac aaa aag ttg gtt ttg ttt tgt gga att     48
Leu Ile Lys Lys Ala Ala Asn Lys Lys Leu Val Leu Phe Cys Gly Ile
1               5                   10                  15 gcg gtg ctt tgg atg tct tta ttt tta acg aat cat aat gat gta cgc     96
Ala Val Leu Trp Met Ser Leu Phe Leu Thr Asn His Asn Asp Val Arg
            20                  25                  30 gcc gat acg atc ggc gag aaa ata gcg gaa act gcc aga cag ctt gag    144
Ala Asp Thr Ile Gly Glu Lys Ile Ala Glu Thr Ala Arg Gln Leu Glu
        35                  40                  45 ggt gcg aaa tac agc tac ggc gga gag aag ccg aaa acg ggg ttt gac    192
Gly Ala Lys Tyr Ser Tyr Gly Gly Glu Lys Pro Lys Thr Gly Phe Asp
    50                  55                  60 tcg tca ggc ttt gtg caa tat gtg ttt caa tcg ctc gat att acg ctt    240
Ser Ser Gly Phe Val Gln Tyr Val Phe Gln Ser Leu Asp Ile Thr Leu
65                  70                  75                  80 ccg aga acg gta aag gaa caa tcg act ctt ggg agc agt gtc ggc cgt    288
Pro Arg Thr Val Lys Glu Gln Ser Thr Leu Gly Ser Ser Val Gly Arg
                85                  90                  95 cag cag ctc gaa aag ggg gac ctt gtc ttt ttc aag aat gcc gag ctg    336
Gln Gln Leu Glu Lys Gly Asp Leu Val Phe Phe Lys Asn Ala Glu Leu
            100                 105                 110 gaa tcg gac gga ccg acc cat gtc gcc atc tat ttg gga aat gat caa    384
Glu Ser Asp Gly Pro Thr His Val Ala Ile Tyr Leu Gly Asn Asp Gln
        115                 120                 125 atc atc cac agc aca aaa tca aac ggg gtt gtc gtg aca aag ctt gaa    432
Ile Ile His Ser Thr Lys Ser Asn Gly Val Val Val Thr Lys Leu Glu
    130                 135                 140 ggc agc tct tac tgg agc tcg ggg tat ttt aaa gcg aaa agg atc aca    480
Gly Ser Ser Tyr Trp Ser Ser Gly Tyr Phe Lys Ala Lys Arg Ile Thr
```

```
                        145                 150                 155                 160
aaa gag cct gag att tcg atg gat cct gtc gtt caa aaa gca aaa agc        528
Lys Glu Pro Glu Ile Ser Met Asp Pro Val Val Gln Lys Ala Lys Ser
                        165                 170                 175 tat gtc ggt gtt cct tat gta ttt gga ggc aac tct ccg gat ctc gga        576
Tyr Val Gly Val Pro Tyr Val Phe Gly Gly Asn Ser Pro Asp Leu Gly
                    180                 185                 190 ttt gac tgt tcg ggg ttg acc caa tac gtc ttc aga gag gtg ctc ggc        624
Phe Asp Cys Ser Gly Leu Thr Gln Tyr Val Phe Arg Glu Val Leu Gly
                195                 200                 205 gtt tat ttg cca agg tcg gct gaa cag caa tgg gct gtc ggt caa aag        672
Val Tyr Leu Pro Arg Ser Ala Glu Gln Gln Trp Ala Val Gly Gln Lys
            210                 215                 220 gtg aag ctt gaa gat atc cgg ccg ggt gat gtt ttg ttt ttc agc aat        720
Val Lys Leu Glu Asp Ile Arg Pro Gly Asp Val Leu Phe Phe Ser Asn
225                 230                 235                 240 acg tac aaa ccg gga ata tcc cat aac ggc atc tat gcc ggg ggc ggg        768
Thr Tyr Lys Pro Gly Ile Ser His Asn Gly Ile Tyr Ala Gly Gly Gly
                        245                 250                 255 cgg ttt atc cat gcg agc cgt tca aat aaa gtg acg ata tcc tac ttg        816
Arg Phe Ile His Ala Ser Arg Ser Asn Lys Val Thr Ile Ser Tyr Leu
                    260                 265                 270 tcg gct tcc tat tgg cag aag aag ttc aca gga gtc aga cgt ttt gac        864
Ser Ala Ser Tyr Trp Gln Lys Lys Phe Thr Gly Val Arg Arg Phe Asp
                275                 280                 285 aac atg tcc ctg cca aaa aat ccg att gta tcc gaa gcc atc agg cat        912
Asn Met Ser Leu Pro Lys Asn Pro Ile Val Ser Glu Ala Ile Arg His
            290                 295                 300 atc ggc gaa gtc ggt tat caa aaa ggc ggc aca tcg cct aaa gaa ggc        960
Ile Gly Glu Val Gly Tyr Gln Lys Gly Gly Thr Ser Pro Lys Glu Gly
305                 310                 315                 320 ttt gat acg gct ggg ttt atc caa tat gtc tac aaa acg gcg gca gga       1008
Phe Asp Thr Ala Gly Phe Ile Gln Tyr Val Tyr Lys Thr Ala Ala Gly
                        325                 330                 335 gtg gag ctt ccg agg tat gct gac aaa caa tac agc acg ggt aag aaa       1056
Val Glu Leu Pro Arg Tyr Ala Asp Lys Gln Tyr Ser Thr Gly Lys Lys
                    340                 345                 350 att acc aaa cag gag ctt gag cct gga gac atc gtc ttc ttt aaa gga       1104
Ile Thr Lys Gln Glu Leu Glu Pro Gly Asp Ile Val Phe Phe Lys Gly
                355                 360                 365 acc act gtt atg aat ccc gcc atc tat atc gga aac ggc cag gtc gtt       1152
Thr Thr Val Met Asn Pro Ala Ile Tyr Ile Gly Asn Gly Gln Val Val
            370                 375                 380 ctt gtc acc ttg tct gcc ggt gta acg aca gca gat atg gag acg agc       1200
Leu Val Thr Leu Ser Ala Gly Val Thr Thr Ala Asp Met Glu Thr Ser
385                 390                 395                 400 gcc tat tgg aaa gat aaa tac gcc gga agc gtc aga att gag tag           1245
Ala Tyr Trp Lys Asp Lys Tyr Ala Gly Ser Val Arg Ile Glu
                        405                 410

<210> SEQ ID NO 10
<211> LENGTH: 414
<212> TYPE: PRT
<213> ORGANISM: Bacillus licheniformis DSM 13

<400> SEQUENCE: 10

Leu Ile Lys Lys Ala Ala Asn Lys Lys Leu Val Leu Phe Cys Gly Ile
1               5                   10                  15

Ala Val Leu Trp Met Ser Leu Phe Leu Thr Asn His Asn Asp Val Arg
            20                  25                  30
```

```
Ala Asp Thr Ile Gly Glu Lys Ile Ala Glu Thr Ala Arg Gln Leu Glu
         35                  40                  45

Gly Ala Lys Tyr Ser Tyr Gly Gly Glu Lys Pro Lys Thr Gly Phe Asp
 50                  55                  60

Ser Ser Gly Phe Val Gln Tyr Val Phe Gln Ser Leu Asp Ile Thr Leu
 65                  70                  75                  80

Pro Arg Thr Val Lys Glu Gln Ser Thr Leu Gly Ser Ser Val Gly Arg
                 85                  90                  95

Gln Gln Leu Glu Lys Gly Asp Leu Val Phe Phe Lys Asn Ala Glu Leu
             100                 105                 110

Glu Ser Asp Gly Pro Thr His Val Ala Ile Tyr Leu Gly Asn Asp Gln
             115                 120                 125

Ile Ile His Ser Thr Lys Ser Asn Gly Val Val Thr Lys Leu Glu
             130                 135                 140

Gly Ser Ser Tyr Trp Ser Ser Gly Tyr Phe Lys Ala Lys Arg Ile Thr
145                 150                 155                 160

Lys Glu Pro Glu Ile Ser Met Asp Pro Val Val Gln Lys Ala Lys Ser
                 165                 170                 175

Tyr Val Gly Val Pro Tyr Val Phe Gly Gly Asn Ser Pro Asp Leu Gly
             180                 185                 190

Phe Asp Cys Ser Gly Leu Thr Gln Tyr Val Phe Arg Glu Val Leu Gly
             195                 200                 205

Val Tyr Leu Pro Arg Ser Ala Glu Gln Gln Trp Ala Val Gly Gln Lys
210                 215                 220

Val Lys Leu Glu Asp Ile Arg Pro Gly Asp Val Leu Phe Phe Ser Asn
225                 230                 235                 240

Thr Tyr Lys Pro Gly Ile Ser His Asn Gly Ile Tyr Ala Gly Gly Gly
                 245                 250                 255

Arg Phe Ile His Ala Ser Arg Ser Asn Lys Val Thr Ile Ser Tyr Leu
             260                 265                 270

Ser Ala Ser Tyr Trp Gln Lys Lys Phe Thr Gly Val Arg Arg Phe Asp
             275                 280                 285

Asn Met Ser Leu Pro Lys Asn Pro Ile Val Ser Glu Ala Ile Arg His
             290                 295                 300

Ile Gly Glu Val Gly Tyr Gln Lys Gly Gly Thr Ser Pro Lys Glu Gly
305                 310                 315                 320

Phe Asp Thr Ala Gly Phe Ile Gln Tyr Val Lys Thr Ala Ala Gly
                 325                 330                 335

Val Glu Leu Pro Arg Tyr Ala Asp Lys Gln Tyr Ser Thr Gly Lys Lys
             340                 345                 350

Ile Thr Lys Gln Glu Leu Glu Pro Gly Asp Ile Val Phe Phe Lys Gly
             355                 360                 365

Thr Thr Val Met Asn Pro Ala Ile Tyr Ile Gly Asn Gly Gln Val Val
             370                 375                 380

Leu Val Thr Leu Ser Ala Gly Val Thr Ala Asp Met Glu Thr Ser
385                 390                 395                 400

Ala Tyr Trp Lys Asp Lys Tyr Ala Gly Ser Val Arg Ile Glu
                 405                 410

<210> SEQ ID NO 11
<211> LENGTH: 1182
<212> TYPE: DNA
<213> ORGANISM: Bacillus subtilis
```

-continued

```
<400> SEQUENCE: 11
atgtggttac tcattatagc ctgtgctgtc atactggtca tcggaatatt agaaaaacga      60
cgacatcaga aaacattga tgccctccct gttcgggtga atattaacgg catccgcgga     120
aaatcgactg tgacaaggct gacaaccgga atattaatag aagccggtta caagactgtt     180
ggaaaaacaa caggaacaga tgcaagaatg atttactggg acacaccgga ggaaaagccg     240
attaaacgga aacctcaggg gccgaatatc ggagagcaaa agaagtcat gagagaaaca      300 gtagaaagag gggctaacgc gattgtcagt gaatgcatgg ctgttaaccc agattatcaa     360
atcatctttc aggaagaact tctgcaggcc aatatcggcg tcattgtgaa tgttttagaa     420
gaccatatgg atgtcatggg gccgacgctt gatgaaattg cagaagcgtt taccgctaca     480
attccttata tggccatct tgtcattaca gatagtgaat ataccgagtt ctttaaacaa      540
aaagcaaaag aacgaaacac aaaagtcatc attgctgata actcaaaaat tacagatgag     600
tatttacgta aatttgaata catggtattc cctgataacg cttctctggc gctgggtgtg     660
gctcaagcac tcggcattga cgaagaaaca gcatttaagg gaatgctgaa tgcgccgcca     720
gatccgggag caatgagaat tcttccgctg atcagtccga gcgagcctgg gcactttgtt     780
aatgggtttg ccgcaaacga cgcttcttct actttgaata tatggaaacg tgtaaaagaa     840
atcggttacc cgaccgatga tccgatcatc atcatgaact gccgcgcaga ccgtgtcgat     900
cggacacagc aattcgcaaa tgacgtattg ccttatattg aagcaagtga actgatctta     960
atcggtgaac aacaagaacc gatcgtaaaa gcctatgaag aaggcaaaat tcctgcagac    1020
aaactgcatg atctagagta taagtcaaca gatgaaatta tggaattgtt aaagaaaaga    1080
atgcacaacc gtgtcatata tggcgtcggc aatattcatg gtgccgcaga gcctttaatt    1140
gaaaaaatcc acgaatacaa ggttaagcag ctcgtaagct ag                        1182

<210> SEQ ID NO 12
<211> LENGTH: 393
<212> TYPE: PRT
<213> ORGANISM: Bacillus subtilis

<400> SEQUENCE: 12

Met Trp Leu Leu Ile Ile Ala Cys Ala Val Ile Leu Val Ile Gly Ile
1               5                   10                  15

Leu Glu Lys Arg Arg His Gln Lys Asn Ile Asp Ala Leu Pro Val Arg
                20                  25                  30

Val Asn Ile Asn Gly Ile Arg Gly Lys Ser Thr Val Thr Arg Leu Thr
            35                  40                  45

Thr Gly Ile Leu Ile Glu Ala Gly Tyr Lys Thr Val Gly Lys Thr Thr
        50                  55                  60

Gly Thr Asp Ala Arg Met Ile Tyr Trp Asp Thr Pro Glu Glu Lys Pro
65                  70                  75                  80

Ile Lys Arg Lys Pro Gln Gly Pro Asn Ile Gly Glu Gln Lys Glu Val
                85                  90                  95

Met Arg Glu Thr Val Glu Arg Gly Ala Asn Ala Ile Val Ser Glu Cys
            100                 105                 110

Met Ala Val Asn Pro Asp Tyr Gln Ile Ile Phe Gln Glu Glu Leu Leu
        115                 120                 125

Gln Ala Asn Ile Gly Val Ile Val Asn Val Leu Glu Asp His Met Asp
    130                 135                 140

Val Met Gly Pro Thr Leu Asp Glu Ile Ala Glu Ala Phe Thr Ala Thr
145                 150                 155                 160
```

```
Ile Pro Tyr Asn Gly His Leu Val Ile Thr Asp Ser Glu Tyr Thr Glu
            165                 170                 175
Phe Phe Lys Gln Lys Ala Lys Glu Arg Asn Thr Lys Val Ile Ile Ala
        180                 185                 190
Asp Asn Ser Lys Ile Thr Asp Glu Tyr Leu Arg Lys Phe Glu Tyr Met
    195                 200                 205
Val Phe Pro Asp Asn Ala Ser Leu Ala Leu Gly Val Ala Gln Ala Leu
210                 215                 220
Gly Ile Asp Glu Glu Thr Ala Phe Lys Gly Met Leu Asn Ala Pro Pro
225                 230                 235                 240
Asp Pro Gly Ala Met Arg Ile Leu Pro Leu Ile Ser Pro Ser Glu Pro
                245                 250                 255
Gly His Phe Val Asn Gly Phe Ala Ala Asn Asp Ala Ser Ser Thr Leu
            260                 265                 270
Asn Ile Trp Lys Arg Val Lys Glu Ile Gly Tyr Pro Thr Asp Asp Pro
        275                 280                 285
Ile Ile Ile Met Asn Cys Arg Ala Asp Arg Val Asp Arg Thr Gln Gln
    290                 295                 300
Phe Ala Asn Asp Val Leu Pro Tyr Ile Glu Ala Ser Glu Leu Ile Leu
305                 310                 315                 320
Ile Gly Glu Gln Gln Glu Pro Ile Val Lys Ala Tyr Glu Glu Gly Lys
                325                 330                 335
Ile Pro Ala Asp Lys Leu His Asp Leu Glu Tyr Lys Ser Thr Asp Glu
            340                 345                 350
Ile Met Glu Leu Leu Lys Lys Arg Met His Asn Arg Val Ile Tyr Gly
        355                 360                 365
Val Gly Asn Ile His Gly Ala Ala Glu Pro Leu Ile Glu Lys Ile His
    370                 375                 380
Glu Tyr Lys Val Lys Gln Leu Val Ser
385                 390

<210> SEQ ID NO 13
<211> LENGTH: 450
<212> TYPE: DNA
<213> ORGANISM: Bacillus subtilis

<400> SEQUENCE: 13
atgttcggat cagatttata catcgcacta attttaggtg tactactcag tttaattttt      60
gcggaaaaaa cagggatcgt gccggcagga ctggttgtac cgggatattt aggacttgtg     120
tttaatcagc cggtctttat tttacttgtt ttgctagtga gcttgctcat ttatgttatc     180
gtgaaatacg gttatccaa atttatgatt ttgtacggac gcagaaaatt tgctgccatg     240
ctgataacag ggatcgtcct aaaaatcgcg tttgattttc tatacccgat tgtaccattt     300
gaaatcgcag aatttcgagg aatcggcatc atcgtgccag gtttaattgc caataccatt     360
cagaaacaag gtttaaccat tacgttcgga agcacgctgc tattgagcgg acgcgccttt     420
gctatcatgt tgtttactta cttaatttaa                                     450

<210> SEQ ID NO 14
<211> LENGTH: 149
<212> TYPE: PRT
<213> ORGANISM: Bacillus subtilis

<400> SEQUENCE: 14

Met Phe Gly Ser Asp Leu Tyr Ile Ala Leu Ile Leu Gly Val Leu Leu
```

```
              1               5              10              15
Ser Leu Ile Phe Ala Glu Lys Thr Gly Ile Val Pro Ala Gly Leu Val
                 20                  25                  30

Val Pro Gly Tyr Leu Gly Leu Val Phe Asn Gln Pro Val Phe Ile Leu
                 35                  40                  45

Leu Val Leu Leu Val Ser Leu Leu Ile Tyr Val Ile Val Lys Tyr Gly
                 50                  55                  60

Leu Ser Lys Phe Met Ile Leu Tyr Gly Arg Arg Lys Phe Ala Ala Met
 65                  70                  75                  80

Leu Ile Thr Gly Ile Val Leu Lys Ile Ala Phe Asp Phe Leu Tyr Pro
                     85                  90                  95

Ile Val Pro Phe Glu Ile Ala Glu Phe Arg Gly Ile Gly Ile Ile Val
                100                 105                 110

Pro Gly Leu Ile Ala Asn Thr Ile Gln Lys Gln Gly Leu Thr Ile Thr
                115                 120                 125

Phe Gly Ser Thr Leu Leu Leu Ser Gly Arg Ala Phe Ala Ile Met Phe
                130                 135                 140

Val Tyr Tyr Leu Ile
145

<210> SEQ ID NO 15
<211> LENGTH: 1143
<212> TYPE: DNA
<213> ORGANISM: Bacillus subtilis

<400> SEQUENCE: 15
atgaaaaaag aactgagctt tcatgaaaag ctgctaaagc tgacaaaaca gcaaaaaaag     60
aaaaccaata agcacgtatt tattgccatt ccgatcgttt ttgtccttat gttcgctttc    120
atgtgggcgg aaaagcgga  aacgccgaag gtcaaaacgt attctgacga cgtactctca    180
gcctcatttg taggcgatat tatgatggga cgctatgttg aaaaagtaac ggagcaaaaa    240
ggggcagaca gtattttttca atatgttgaa ccgatcttta gagcctcgga ttatgtagca    300
ggaaactttg aaaacccggt aacctatcaa aagaattata acaagcaga  taaagagatt    360
catctgcaga cgaataagga tcagtgaaa  gtcttgaagg atatgaattt cacggttctc    420
aacagcgcaa acaaccacgc aatggattac ggcgttcagg gcatgaaaga tacgcttgga    480
gaatttgcga cgaaaaacct tgatatcgtt ggagcgggat acagcttaag tgatgcgaaa    540
aagaaaattt cgtaccagaa agtcaacggg gtaacgattg cgacgcttgg ctttaccgat    600
gtgtccggga aggtttcgc  ggctaaaaag aatacgccgg cgtgctgcc  cgcagatcct    660
gaaatcttca tccctatgat ttcagaagcg aaaaaacatg ctgacattgt tgttgtgcag    720
tcacactggg ccaagagta  tgacaatgat ccaaacgacc gccagcgcca gcttgcaaga    780
gccatgtctg atgcgggagc tgacatcatc gtcggccatc atccgcacgt cttagaaccg    840
attgaagtat ataacggaac cgtcattttc tacagcctcg gcaactttgt ctttgaccaa    900
ggctggacga gaacaagaga cagtgcactg gttcagtatc acctgaagaa aaatggaaca    960
ggccgctttg aagtgacacc gatcgatatc catgaagcga cacctgcacc tgtgaaaaaa   1020
gacagcctta acagaaaac  cattattcgc gaactgacga agactctaa  tttcgcttgg   1080
aaagtagaag acgaaaaact gacgtttgat attgatcata gtgacaaact aaaatctaaa   1140
taa                                                                  1143

<210> SEQ ID NO 16
```

<211> LENGTH: 380
<212> TYPE: PRT
<213> ORGANISM: Bacillus subtilis

<400> SEQUENCE: 16

```
Met Lys Lys Glu Leu Ser Phe His Glu Lys Leu Leu Lys Leu Thr Lys
1               5                   10                  15

Gln Gln Lys Lys Lys Thr Asn Lys His Val Phe Ile Ala Ile Pro Ile
            20                  25                  30

Val Phe Val Leu Met Phe Ala Phe Met Trp Ala Gly Lys Ala Glu Thr
        35                  40                  45

Pro Lys Val Lys Thr Tyr Ser Asp Asp Val Leu Ser Ala Ser Phe Val
    50                  55                  60

Gly Asp Ile Met Met Gly Arg Tyr Val Glu Lys Val Thr Glu Gln Lys
65                  70                  75                  80

Gly Ala Asp Ser Ile Phe Gln Tyr Val Glu Pro Ile Phe Arg Ala Ser
                85                  90                  95

Asp Tyr Val Ala Gly Asn Phe Glu Asn Pro Val Thr Tyr Gln Lys Asn
            100                 105                 110

Tyr Lys Gln Ala Asp Lys Glu Ile His Leu Gln Thr Asn Lys Glu Ser
        115                 120                 125

Val Lys Val Leu Lys Asp Met Asn Phe Thr Val Leu Asn Ser Ala Asn
    130                 135                 140

Asn His Ala Met Asp Tyr Gly Val Gln Gly Met Lys Asp Thr Leu Gly
145                 150                 155                 160

Glu Phe Ala Thr Lys Asn Leu Asp Ile Val Gly Ala Gly Tyr Ser Leu
                165                 170                 175

Ser Asp Ala Lys Lys Ile Ser Tyr Gln Lys Val Asn Gly Val Thr
            180                 185                 190

Ile Ala Thr Leu Gly Phe Thr Asp Val Ser Gly Lys Gly Phe Ala Ala
        195                 200                 205

Lys Lys Asn Thr Pro Gly Val Leu Pro Ala Asp Pro Glu Ile Phe Ile
    210                 215                 220

Pro Met Ile Ser Glu Ala Lys Lys His Ala Asp Ile Val Val Val Gln
225                 230                 235                 240

Ser His Trp Gly Gln Glu Tyr Asp Asn Asp Pro Asn Asp Arg Gln Arg
                245                 250                 255

Gln Leu Ala Arg Ala Met Ser Asp Ala Gly Ala Asp Ile Ile Val Gly
            260                 265                 270

His His Pro His Val Leu Glu Pro Ile Glu Val Tyr Asn Gly Thr Val
        275                 280                 285

Ile Phe Tyr Ser Leu Gly Asn Phe Val Phe Asp Gln Gly Trp Thr Arg
    290                 295                 300

Thr Arg Asp Ser Ala Leu Val Gln Tyr His Leu Lys Lys Asn Gly Thr
305                 310                 315                 320

Gly Arg Phe Glu Val Thr Pro Ile Asp Ile His Glu Ala Thr Pro Ala
                325                 330                 335

Pro Val Lys Lys Asp Ser Leu Lys Gln Lys Thr Ile Ile Arg Glu Leu
            340                 345                 350

Thr Lys Asp Ser Asn Phe Ala Trp Lys Val Glu Asp Gly Lys Leu Thr
        355                 360                 365

Phe Asp Ile Asp His Ser Asp Lys Leu Lys Ser Lys
    370                 375                 380
```

<210> SEQ ID NO 17
<211> LENGTH: 1242
<212> TYPE: DNA
<213> ORGANISM: Bacillus subtilis

<400> SEQUENCE: 17

```
gtgaacacac tggcaaactg aagaagttt ttgcttgtgg cggttatcat ttgttttttg      60
gttccaatta tgacaaaagc ggagattgcg gaagctgata catcatcaga attgattgtc     120
agcgaagcaa aaaacctgct tggatatcag tataaatatg gcggggaaac gccgaaagag     180
ggtttcgatc catcaggatt gatacaatat gtgttcagta aggctgatat tcatctgccg     240
agatctgtaa acgaccagta taaaatcgga acagctgtaa agccggaaaa cctgaagccg     300
ggtgatattt tgttttttcaa gaagaggga agcaacggct ctgttccgac acatgacgcc     360
ctttatatcg gagacggcca aatggtacac agtacacagt caaaaggggt tatcatcacc     420
aattacaaaa aaagcagcta ttggagcgga acttatatcg gagcgagacg aatcgctgcc     480
gatccggcaa cggctgatgt tcctgtcgtt caggaggccg aaaaatatat cggtgtccca     540
tatgtgtttg gcggaagcac gccgtcagag ggctttgatt gctcgggggct tgtgcaatat     600
gtgtttcaac aggcactcgg catttatctg ccgcgatcag ccgaacagca gtgggcagtg     660
ggcgagaaga tagcccctca gaacataaag cctggtgatg tcgtctattt cagcaatacg     720
tataaaacgg gaatttcaca tgcaggcatt tatgcgggcg caggcaggtt catccaggcg     780
agcaggtcag aaaaagtaac catttcctat ttgtcagagg attactgaa atcgaagatg     840
acgggtattc gccgatttga caacctgaca atcccgaaaa aaaatccgat tgtttccgaa     900
gcgacgcttt atgtcggaga agtgccttac aaacagggcg gagtaacacc tgagacagga     960
tttgatacag ctggatttgt ccaatatgta taccagaaag cagccggtat ttccctgcct    1020
cgatacgcaa caagccagta caatgccgga actaagatta agaaggcgga cctgaagccg    1080
ggagacattg tgttctttca atcaacaagc ttaaatccct ccatctatat cggaaacgga    1140
caagttgttc atgtcacatt atcaaacggc gtgaccatca ccaatatgaa cacgagcaca    1200
tattggaagg ataaatacgc aggaagtata cgggtgcaat aa                      1242
```

<210> SEQ ID NO 18
<211> LENGTH: 413
<212> TYPE: PRT
<213> ORGANISM: Bacillus subtilis

<400> SEQUENCE: 18

```
Met Asn Thr Leu Ala Asn Trp Lys Lys Phe Leu Leu Val Ala Val Ile
1               5                   10                  15

Ile Cys Phe Leu Val Pro Ile Met Thr Lys Ala Glu Ile Ala Glu Ala
            20                  25                  30

Asp Thr Ser Ser Glu Leu Ile Val Ser Glu Ala Lys Asn Leu Leu Gly
        35                  40                  45

Tyr Gln Tyr Lys Tyr Gly Gly Glu Thr Pro Lys Glu Gly Phe Asp Pro
    50                  55                  60

Ser Gly Leu Ile Gln Tyr Val Phe Ser Lys Ala Asp Ile His Leu Pro
65                  70                  75                  80

Arg Ser Val Asn Asp Gln Tyr Lys Ile Gly Thr Ala Val Lys Pro Glu
                85                  90                  95

Asn Leu Lys Pro Gly Asp Ile Leu Phe Phe Lys Lys Glu Gly Ser Asn
            100                 105                 110

Gly Ser Val Pro Thr His Asp Ala Leu Tyr Ile Gly Asp Gly Gln Met
```

-continued

```
            115                 120                 125
Val His Ser Thr Gln Ser Lys Gly Val Ile Ile Thr Asn Tyr Lys Lys
        130                 135                 140

Ser Ser Tyr Trp Ser Gly Thr Tyr Ile Gly Ala Arg Arg Ile Ala Ala
145                 150                 155                 160

Asp Pro Ala Thr Ala Asp Val Pro Val Val Gln Glu Ala Glu Lys Tyr
                165                 170                 175

Ile Gly Val Pro Tyr Val Phe Gly Gly Ser Thr Pro Ser Glu Gly Phe
                180                 185                 190

Asp Cys Ser Gly Leu Val Gln Tyr Val Phe Gln Ala Leu Gly Ile
                195                 200                 205

Tyr Leu Pro Arg Ser Ala Glu Gln Gln Trp Ala Val Gly Glu Lys Ile
        210                 215                 220

Ala Pro Gln Asn Ile Lys Pro Gly Asp Val Val Tyr Phe Ser Asn Thr
225                 230                 235                 240

Tyr Lys Thr Gly Ile Ser His Ala Gly Ile Tyr Ala Gly Ala Gly Arg
                245                 250                 255

Phe Ile Gln Ala Ser Arg Ser Glu Lys Val Thr Ile Ser Tyr Leu Ser
                260                 265                 270

Glu Asp Tyr Trp Lys Ser Lys Met Thr Gly Ile Arg Arg Phe Asp Asn
        275                 280                 285

Leu Thr Ile Pro Lys Glu Asn Pro Ile Val Ser Glu Ala Thr Leu Tyr
        290                 295                 300

Val Gly Glu Val Pro Tyr Lys Gln Gly Gly Val Thr Pro Glu Thr Gly
305                 310                 315                 320

Phe Asp Thr Ala Gly Phe Val Gln Tyr Val Tyr Gln Lys Ala Ala Gly
                325                 330                 335

Ile Ser Leu Pro Arg Tyr Ala Thr Ser Gln Tyr Asn Ala Gly Thr Lys
                340                 345                 350

Ile Lys Lys Ala Asp Leu Lys Pro Gly Asp Ile Val Phe Phe Gln Ser
        355                 360                 365

Thr Ser Leu Asn Pro Ser Ile Tyr Ile Gly Asn Gly Gln Val Val His
        370                 375                 380

Val Thr Leu Ser Asn Gly Val Thr Ile Thr Asn Met Asn Thr Ser Thr
385                 390                 395                 400

Tyr Trp Lys Asp Lys Tyr Ala Gly Ser Ile Arg Val Gln
                405                 410
```